(12) United States Patent
Zhang et al.

(10) Patent No.: US 7,807,464 B2
(45) Date of Patent: Oct. 5, 2010

(54) METHODS FOR EXPANSION AND ANALYSIS OF CULTURED HEMATOPOIETIC STEM CELLS

(75) Inventors: Chengcheng Zhang, Arlington, MA (US); Harvey F. Lodish, Brookline, MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 509 days.

(21) Appl. No.: 11/438,847

(22) Filed: May 23, 2006

(65) Prior Publication Data
US 2007/0020757 A1    Jan. 25, 2007

Related U.S. Application Data

(60) Provisional application No. 60/753,212, filed on Dec. 22, 2005, provisional application No. 60/684,147, filed on May 24, 2005.

(51) Int. Cl.
C12N 5/00     (2006.01)

(52) U.S. Cl. .................. 435/377; 435/325; 435/375

(58) Field of Classification Search .................. None
See application file for complete search history.

(56) References Cited

U.S. PATENT DOCUMENTS

| 5,004,681 | A | * | 4/1991 | Boyse et al. ............... 435/2 |
| 2002/0177227 | A1 | | 11/2002 | Kraus et al. ............... 435/366 |
| 2004/0157326 | A1 | | 8/2004 | Miura et al. |
| 2005/0032122 | A1 | | 2/2005 | Hwang et al. |
| 2005/0276793 | A1 | | 12/2005 | Milhem et al. |
| 2006/0115898 | A1 | | 6/2006 | Zhang et al. |

FOREIGN PATENT DOCUMENTS

| EP | 0 962 530 A2 | 12/1999 |
| EP | 1 308 511 A1 | 5/2003 |
| WO | WO 00/52167 | 9/2000 |
| WO | 02/083845 | 10/2002 |

OTHER PUBLICATIONS

Kumar D et al. 2005. Transforming growth factor-beta 2 enhances differentiation of cardiac myocytes from embryonic stem cells. Biochem Biophys Res Comm 332: 135-141.*
Bauvois B et al. 1996. TGF-beta1-stimulated adhesion of human mononuclear phagocytes to fibronectin and laminin is abolished by IFN-gamma: Dependence on alpha5beta1 and beta2 integrins. Exp Cell Res 222: 209-217.*
Turley J et al. 1996. Transforming growth factor beta1 functions in monocytic differentiation of hematopoietic cells through autocrine and paracrine mechanisms. Cell Growth Different 7: 1535-1544.*
Liao R. 2005. Yin and yang of myocardial transforming growth factor-beta1: timing is everything. Circulation 111: 2416-2417.*
Huang X-L et al. 1999. In vitro effects of angiopoietins and VEGF on hematopoietic and endothelial cells. Biochem Biophys Res Comm 264: 133-138.*
Kim I et al. 1999. Molecular cloning and characterization of a novel angiopoietin family protein, angiopoietin-3. FEBS Lett 443: 353-356.*

Antonchuk, J. et al., "HOXB4-Induced Expansion of Adult Hematopoietic Stem Cells Ex Vivo," *Cell*, vol. 109, pp. 39-45 (2002).
Arai, F. et al., "Tie2/Angiopoietin-1 Signaling Regulates Hematopoietic Stem Cell Quiescence in the Bone Marrow Niche," *Cell*, vol. 118, pp. 149-161 (2004).
Baumann, C.I. et al., "PECAM-1 is expressed on hematopoietic stem cells throughout ontogeny and identifies a population of erythroid progenitors," *Blood*, vol. 104, No. 4, pp. 1010-1016 (2004).
Breems et al., "Frequency Analysis of Human Primitive Haematopoietic Stem Cell Subsets Using a Cobblestone Area Forming Cell Assay," *Leukemia*, 8:1095-1104 (1994).
Bunting, K.D. et al., "Effects of Retroviral-Mediated MDR1 Expression on Hematopoietic Stem Cell Self-Renewal and Differentiation in Culture$^a$," *Ann. N.Y. Acad. Sci.*, vol. 872, pp. 125-140 (1999).
Camargo, F.D. et al., "Single Hematopietic Stem Cells Generate Skeletal Muscle Through Myeloid Intermediates," *Nat Med*, 9:1520-7 (2003).
Camenisch et al., "ANGPTL3 Stimulates Endothelial Cell Adhesion and Migration via Integrin $\alpha_v\beta_3$ and Induces Blood Vessel Formation in Vivo," *The Journal of Biological Chemistry*, vol. 277, No. 19, pp. 17281-17290 (2002).
Chen, C.Z. et al., "The Endoglin $^{Positive}$ Sca-1 $^{Positive}$ Rhodamine $^{Low}$ Phenotype Defines a near-Homogeneous Population of Long-Term Repopulating Hematopoietic Stem Cells," *Immunity*, vol. 19, pp. 525-533 (2003).
Cipolleschi, M. et al., "The Rolse of Hypoxia in the Maintenance of Hematopoietic Stem Cells," *Blood*, vol. 82, No. 7, pp. 2031-2037 (1993).
Conklin, D. et al., "Identification of a Mammalian Angiopoietin-Related Protein Expressed Specifically in Liver," *Genomics*, 62:477-82 (1999).
Craig, et al. , "Expression of Thy-1 on Human Hematopoietic Progenitor Cells," *J. Exp. Med.*, vol. 177, pp. 1331-1342 (1993).
Cwirla et al., "Peptide Agonist of the Thrombopoietin Receptor as Potent as the Natural Cytokine," *Science*, 276:1696-1698 (1997).
de Haan, G. et al., "In Vitro Generation of Long-Term Repopulating Hematopoietic Stem Cells by Fibroblast Growth Factor-1," *Developmental Cell*, vol. 4, pp. 241-251 (2003).
Devine, S.M. et al., "Clinical application of hematopoietic progenitor cell expansion: current status and future prospects," *Bone Marrow Transplantation*, 31, pp. 241-252 (2003).
Domen, J. et al., "Self-renewal, differentiation or death: regulation and manipulation of hematopoietic stem cell fate," *Molecule Medicine Today*, vol. 5, pp. 201-208 (1999).
Fraser, C.C. et al., "Expansion In vitro of Retrovirally Marked Totipotent Hematopoietic Stem Cells," *Blood*, vol. 76, No. 6, pp. 1071-1076 (1990).

(Continued)

*Primary Examiner*—Lora E Barnhart
(74) *Attorney, Agent, or Firm*—Proskauer Rose LLP

(57) ABSTRACT

Methods and kits for propagating hematopoietic stem cells are provided. The methods comprise culturing cells in medium comprising one or more angiopoietin-like proteins, under conditions sufficient for expansion of HSCs. Angiopoietin-like proteins include angiopoietin-like protein 2, angiopoietin-like protein 3, angiopoietin-like protein 4, angiopoietin-like protein 5, angiopoietin-like protein 7, and microfibrillar-associated glycoprotein (Mfap4). Methods for identifying hematopoietic stem cells are provided and isolated hematopoietic stem cells are also provided.

39 Claims, 18 Drawing Sheets

OTHER PUBLICATIONS

Goodell, M.A., et al., "Isolation and Functional Properties of Murine Hematopoietic Stem Cells that are Replicating In Vivo," *J. Exp. Med.*, vol. 183, pp. 1797-1806 (1996).
Gussoni, E. et al., "Dystrophin Expression in the Mdx Mouse Restored by Stem Cell Transplantation," *Nature*, 401:390-394 (1999).
Henniker, A.J., "CD24," *J. Biol Regulators and Homeostatic Agents*, 15, pp. 182-184 (2001).
Issaragrishi, S. et al., Brief Report: Transplantation of Cord-Blood Stem Cells into a Patient with Severe Thalassemia, *The New England Journal of Medicine*, vol. 332, No. 6, pp. 367-369 (1995).
Kim, I. et al., "Molecular Cloning, Expression, and Characterization of Angiopoietin-Related Protein," *The Journal of Biological Chemistry*, vol. 274, No. 37, pp. 26528-1999 (1999).
Koishi, R. et al., "Angptl3 Regulates Lipid Metabolism in Mice," *Nat Genet*, 30:151-7 (2002).
Kondo, M. et al., "Biology of Hematopoietic Stem Cells and Progenitors: Implications for Clinical Application," *Annu. Rev. Immunol.*, 21, pp. 759-806 (2003).
Krosl, J. et al., "In Vitro Expansion of Hematopoietic Stems Cells by Recombinant TAT-HOXB4 Protein," *Nat Med*, 9:1428-32 (2003).
Kyoizumi et al., "Implantation and Maintenance of Functional Human Bone Marrow in SCID-hu Mice," *Blood*, 79:1704-1711 (1992).
Li, C.L. et al., "Stem Cell Factor Enhances the Survival But Not the Self-Renewal of Murine Hematopoietic Long-Term Repopulating Cells," *Blood*, vol. 84, No. 12, pp. 408-414 (1994).
Matsunaga, T. et al., "Thrombopoietin Promotes the Survival of Murine Hematopoietic Long-Term Reconstituting Cells: Comparison With the Effects of FLT3/FLK-2 Ligand and Interleukin-6," *Blood*, vol. 92, No. 2, pp. 452-461 (1998).
Miller, C.L. et al., "Expansion in vitro of adult murine hematopoietic stem cells with transplantable lmph-myeloid reconstituting ability," *Proc. Natl. Acad. Sci. USA*, vol. 94, pp. 13648-13653 (1997).
Miyagi, T. et al., "Flk1 + cells derived from mouse embryonic stem cells reconstitute hematopoiesis in vivo in SCID mice," *Exper. Hematology*, vol. 30, pp. 1444-1453 (2002).
Moore, K.A. et al., "In Vitro Maintenance of Highly Purified, Transplantable Hematopoietic Stem Cells," *Blood*, vol. 89, No. 12, pp. 4337-4347 (1997).
Moore, T. et al., "Expression of CD43 on Murine and Human Pluripotent Hematopoietic Stem Cells[1]," *The Journal of Immunology*, 153, pp. 4978-4987 (1994).
Murray et al., "Enrichment of Human Hematopoietic Stem Cell Activity in the CD34+Thy-1+Lin Subpopulation From Mobilized Peripheral Blood," *Blood*, 85:368-378 (1995).
Oike et al., "Angiopoietin-Related/Angiopoietin-Like Proteins Regulation Angiogenesis," *Int. J. Hematol.*, 80:21-28 (2004).
Orschell-Traycoff, C.M. et al., "Homing and engraftment potential of Sca-1+ in− cells fractionated on the basis of adhesion molecule expression and position in cell cycle," *Blood*, vol. 96, No. 4, pp. 1380-1387 (2000).
Osawa, M. et al., "Long-Term Lymphohematopoietic Reconstitution by a Single C34-Low/Negative Hematopoietic Stem Cell," *Science*, vol. 273, No. 5272, pp. 242-245 (1996).
Owen, M. "Marrow Derived Stromal Stem Cells," *J. Cell Science Supp.*, 10:63-76 (1988).
Peled, A. et al., "Dependence of Human Stem Cell Engraftment and Repopulation of NOD/SCID Mice on CXCR4," *Science*, vol. 283, pp. 845-848 (1999).
Pittenger, M.F. et al., "Mesenchymal Stem Cells of Human Adult Bone Marrow," Cold Spring Harbor, New York: *Cold Spring Harbor Laboratory Press*, 349-374 (2001).
Reya, T. et al., "A role for Wnt signaling in sef-renewal of haematopoietic stem cells," *Nature*, 423, pp. 409-414 (2003).
Sato, T. et al., "Reversible Expression of CD34 by Murine Hematopoietic Stem Cells," *Blood*, vol. 94, No. 8, pp. 2548-2554 (1999).
Sauvageau, G. et al., "In Vitro and In Vivo Expansion of Hematopoietic Stem Cells," *Oncogene*, 23:7223-32 (2004).
Shi, Q. et al., "Evidence for Circulating Bone Marrow-Derived Endothelial Cells," *Blood*, vol. 92, No. 2, pp. 362-367 (1998).
Shizuru, J.A., et al., "Hematopoietic Stem and Progenitor Cells: Clinical and Preclinical Regeneration of the Hematolymphoid System," *Annu. Rev. Med.*, 56, pp. 509-538 (2005).
Sitnicka, E. et al., "The effect of Thrombopoietin on the Proliferation and Differentiation of Murine Hematopoietic Stem Cells," *Blood*, vol. 87, No. 12, pp. 4998-5005 (1996).
Solar, G.P. et al., "Role of c-mpl in Early Hematopoiesis," *Blood*, vol. 92, No. 1, pp. 4-10 (1998).
Sorentino, B.P., "Clinical Strategies for Expansion of Hematopoietic Stem Cells," *Nat Rev Immunol*, 4:878-88 (2004).
Spangrude, G.J. et al., "Purification and Characterization of Mouse Hematopoietic Stem Cells," *Science*, vol. 241, No. 4861, pp. 58-62 (1988).
Srour et al., "Animal Models for Human Hematopoiesis," *J. Hematother.*, 1:143-153 (1992).
Sutherland, H.J. et al., "Functional Characterization of Individual Human Hematopoietic Stem Cells Cultured at Limiting Dilution on Supportive Marrow Stromal Layers," *Proc. Natl. Acad Sci. USA*, vol. 87, pp. 3584-3588 (1990).
Valenzuela, D.M. et al., "Angiopoietins 3 and 4: Diverging Gene Counterparts in Mice and Humans," *Proc. Natl. Acad. Sci. USA*, vol. 96, pp. 1904-1909 (1999).
Varnum-Finney, B. et al., "Pluripotent, cytokine-dependent, hematopoietic stem cells are immortalized by constitutive Notch 1 signaling," *Nature Medicine*, vol. 6, No. 11, pp. 1278-1281 (2000).
Willert, K. et al., "Wnt Proteins are Lipid-Modified and Can Act as Stem Growth Factors," *Nature*, 423:448-52 (2003).
Yagi, M. et al., "Sustained ex vivo expansion of hematopoietic stem cells mediated by thrombopoietin," *Proc. Natl. Acad. Sci. USA*, vol. 96, pp. 8126-8131 (1999).
Yin, A. et al., "AC133, a Novel Marker for Human Hematopoietic Stem and Progenitor Cells," *Blood*, vol. 90, No. 12, pp. 5002-5012 (1997).
Zanjani et al., "Engraftment and Long-Term Expression of Human Fetal Hemopoietic Stem Cells in Sheep Following Transplantation in Utero," *J. Clin. Invest.*, 89:1178-1188 (1992).
Zhang, C.C., et al., "Insulin-like growth factor 2 expressed in a novel fetal liver cell population is a growth factor for hematopoietic stem cells," *Blood*, vol. 103, No. 7, pp. 2513-2521 (2004).
Zhang, C.C., et al., "Murine hematopoietic stem cells change their surface phenotype during ex vivo expansion," *Blood*, vol. 105, No. 11, pp. 4314-4320 (2005).
Zeng, L. et al., "Identification of a Novel Human Angiopoietin-Like Gene Expressed Mainly in Heart," *J Hum Genet*, 48:159-62 (2003).
Chen, Chang-Zheng, et al., "Identification of endoglin as a functional marker that defines long-term repopulating hematopoietic stem cells," *Proceedings of the National Academy of Sciences of the United States of America*, vol. 99, No. 24, pp. 15468-15473 (2002).
Choong, Meng Ling, et al., "A novel role for proliferin-2 in the ex vivo expansion of hematopoietic stem cells," *FEBS Letters*, vol. 550, pp. 155-162 (2003).
Zhang, Cheng Cheng, et al., "Angiopoietin-like proteins stimulate ex vivo expansion of hematopoietic stem cells," *Nature Medicine*, vol. 12, No. 2, pp. 240-245 (2006).
International Search Report for International Application No. PCT/US2006/020078, date of mailing Apr. 12, 2006.
Dawczynski, K., et al. "Changes of serum growth factors (IGF-I,-II and IGFBP-2,-3) prior to and after stem cell transplantation in children with acute leukemia." *Bone Marrow Transplantation*, vol. 32, pp. 411-415 (2003).
Huynh, H., et al., "Insulin-like growth factor-binding protein 2 secreted by a tumorigenic cell line supports ex vivo expansion of mouse hematopoietic stem cells." *Stem Cells* (Miamisburg), vol. 26, pp. 1628-1635 (2008).
Liu, L., et al., "Functional cloning of IGFBP-3 from human microvascular endothelial cells reveals its novel role in promoting proliferation of primitive CD34+CD38-hematopoietic cells in vitro." *Oncology Research*, vol. 13, pp. 359-371 (2003).
Zhang, C., et al., "Angiopoietin-like 5 and IGFBP2 stimulate ex vivo expansion of human cord blood hematopoietic stem cells as assayed by NOD/SCID transplantation." *Blood*, vol. 111, pp. 3415-3423 (2008).

* cited by examiner

FIG. 15

SEQ ID NO: 3

```
  1 mrplcvtcww lgllaamgav agqedgfegt eegsprefiy lnrykrages qdkctytfiv
 61 pqqrvtgaic vnskepevll enrvhkqele llnnellkqk rqietlqqlv evdggivsev
121 kllrkesrnm nsrvtqlymq llheiirkrd nalelsqlen rilnqtadml qlaskykdle
181 hkyqhlatla hnqseiiaql eehcqrvpsa rpvpqpppaa pprvyqppty nriinqistn
241 eiqsdqnlkv lppplptmpt ltslpsstdk psgpwrdclq aledghdtss iylvkpentn
301 rlmqvwcdqr hdpggwtviq rrldgsvnff rnwetykqgf gnidgeywlg leniywltnq
361 gnykllvtme dwsgrkvfae yasfrlepes eyyklrlgry hgnagdsftw hngkqfttld
421 rdhdvytgnc ahyqkggwwy nacahsnlng vwyrgghyrs ryqdgvywae frggsyslkk
481 vvmmirpnpn tfh
```

SEQ ID NO: 4

```
  1 mftiklllfi vplvissrid qdnssfdsls pepksrfaml ddvkilangl lqlghglkdf
 61 vhktkgqind ifqklnifdq sfydlslqts eikeeekelr rttyklqvkn eevknmslel
121 nsklesllee killqqkvky leeqltnliq nqpetpehpe vtslktfvek qdnsikdllq
181 tvedqykqln qqhsqikeie nqlrrtsiqe pteislsskp raprttpflq lneirnvkhd
241 gipaecttiy nrgehtsgmy airpsnsqvf hvycdvisgs pwtliqhrid gsqnfnetwe
301 nykygfgrld gefwlgleki ysivkqsnyv lrieledwkd nkhyieysfy lgnhetnytl
361 hlvaitgnvp naipenkdlv fstwdhkakg hfncpegysg gwwwhdecge nnlngkynkp
421 rakskperrr glswksqngr lysikstkml ihptdsesfe
```

SEQ ID NO: 5

```
  1 msgaptagaa lmlcaatavl lsaqggpvqs ksprfaswde mnvlahgllq lgqglrehae
 61 rtrsqlsale rrlsacgsac qgtegstdlp lapesrvdpe vlhslqtqlk aqnsriqqlf
121 hkvaqqqrhl ekqhlriqhl qsqfglldhk hldhevakpa rrkrlpemaq pvdpahnvsr
181 lhrlprdcqe lfqvgerqsg lfeiqpqgsp pflvnckmts dggwtviqrr hdgsvdfnrp
241 weaykagfgd phgefwlgle kvhsitgdrn srlavqlrdw dgnaellqfs vhlggedtay
301 slqltapvag qlgattvpps glsvpfstwd qdhdlrrdkn cakslsggww fgtcshsnln
361 gqyfrsipqq rqklkkgifw ktwrgryypl qattmliqpm aaeaas
```

SEQ ID NO: 6

```
  1 mmspsqasll flnvcificg eavqgncvhh stdssvvniv edgsnakdes ksndtvcked
 61 ceescdvktk itreekhfmc rnlqnsivsy trstkkllrn mmdeqqasld ylsnqvnelm
121 nrvllittev frkqldpfph rpvqshgldc tdikdtigsv tktpsglyii hpegssypfe
181 vmcdmdyrgg gwtviqkrid giidfqrlwc dyldgfgdll gefwlglkki fyivnqknts
241 fmlyvalese ddtlayasyd nfwledetrf fkmhlgrysg nagdafrglk kednqnampf
301 stsdvdndgc rpaclvngqs vkscshlhnk tgwwfnecgl anlngihhfs gkllatgiqw
361 gtwtknnspv kiksvsmkir rmynpyfk
```

METHODS FOR EXPANSION AND ANALYSIS OF CULTURED HEMATOPOIETIC STEM CELLS

RELATED APPLICATIONS

This application claims the benefit of U.S. Provisional Patent Application Ser. No. 60/753,212 filed on Dec. 22, 2005 and the benefit of U.S. Provisional Patent Application Ser. No. 60/684,147 filed on May 24, 2005, the teachings of which are incorporated herein in their entireties.

GOVERNMENT FUNDING

This invention was made with support from the United States government under grant numbers R01 DK 067356-01 and 075/P-IRFT, awarded by the National Institutes of Health, and the United States government has certain rights in the invention.

BACKGROUND OF THE INVENTION

The hematopoietic stem cell (HSC) through proliferation and differentiation gives rise to all of the cells in the hematopoietic system. Pluripotent HSCs are considered to be ideal candidates for disease therapy and they serve as attractive target cells for delivery of genes and gene products. It is desirable to have access to large amounts of such HSCs; unfortunately, hematopoietic stem cells are present in extremely low numbers in tissues where they are found, such as bone marrow and cord blood. Therefore, there is a need for improved methods of ex vivo cell culture systems capable of expanding hematopoietic cells, while maintaining stem cell pluripotency. It is also important to be able to readily identify cells retaining such pluripotency.

Difficulties in ex vivo expansion of HSCs have greatly hampered their clinical utility as well as studies of their biological properties. The identification of new protein factors that can stimulate the self-renewal or prevent their apoptosis is an essential way to increase the number of HSCs, including long term HSCs (LT-HSCs) in culture.

SUMMARY

As described herein, angiopoietin-like proteins promote the expansion of HSCs. As a result of the present invention, hematopoietic stem cells can be expanded to greater numbers in vitro.

The present invention includes methods of propagating hematopoietic stem cells in vitro comprising culturing one or more cells in culture medium comprising an angiopoietin-like protein, wherein at least one of the cells is capable of differentiating into one or more blood cell types. In an embodiment, a population of cells that contains stem cells is cultured in a medium that contains an effective amount of one or more angiopoietin-like proteins under conditions sufficient for expansion of the cells. In a more particular embodiment, the method of propagating hematopoietic stem cells comprises culturing one or more primary cells for at least five days in a serum free culture medium comprising an angiopoietin-like protein. The angiopoietin-like protein can be, for example, angiopoietin-like protein 2, angiopoietin-like protein 3, angiopoietin-like protein 4, angiopoietin-like protein 5, angiopoietin-like protein 7, or Mfap4. In another embodiment, the method of propagating hematopoietic stem cells comprises culturing at least one primary cell for at least five days in a serum free culture medium comprising an angiopoietin-like protein selected from the group consisting of angiopoietin-like protein 2, angiopoietin-like protein 3, angiopoietin-like protein 4, angiopoietin-like protein 5, angiopoietin-like protein 7, or Mfap4, wherein at least one of the primary cells is capable of differentiating into one or more blood cell types. In still another embodiment, the method of propagating hematopoietic stem cells comprises culturing at least one human cell for at least five days in a serum free culture medium comprising angiopoietin-like protein 5, wherein at least one of the human cells is capable of differentiating into one or more blood cell types.

Cultured stem cells of the invention include hematopoietic stem cells, endothelial progenitor cells, bone marrow stromal stem cells, mesenchymal stem cells, embryonic stem (ES) cells and skeletal muscle stem cells. Hematopoietic stem cells are particularly preferred.

HSCs can be cultured from any cell or population of cells which contains or has the potential to develop into HSCs. The population of cells can contain at least 0.1% hematopoietic stem cells. In an embodiment, the one or more cells are primary cells. Typically, primary cells are obtained directly from tissue. Methods of obtaining primary cells are well known in the art.

In another embodiment, the one or more cells can comprise total bone marrow, umbilical cord blood cells, mobilized peripheral blood stem cells, or fetal liver cells. In another embodiment, the one or more cells comprises side population (SP) cells. In still another embodiment, the one or more cells comprises an isolated population of SP Sca1$^+$ CD45$^+$ bone marrow cells. In other embodiments, the population of cells cultured can comprise CD34$^+$ umbilical cord blood cells, AC133$^+$ (prominin) umbilical cord blood cells, CD34$^+$ mobilized peripheral blood stem cells, or AC133$^+$ mobilized peripheral blood stem cells. In still another embodiment, the one or more cells can be human bone marrow CD34$^+$ and AC133$^+$ cells. Other enriched populations of hematopoietic stem cells can be used. Embryonic stem cells can also be used.

The one or more cells can be cultured for at least five days. In other embodiments, the one or more cells can be cultured for at least 10 days, or at least 2 weeks, or for at least four weeks.

The culture medium used for culturing the cells can comprise serum-free medium. The culture medium can comprise an effective amount of one or more additional factor(s), such as a cytokine(s). Suitable factors include insulin-like growth factor (IGF) and at least one of fibroblast growth factor (FGF), thrombopoietin (TPO), and stem cell factor (SCF), under conditions sufficient for expansion of the cells. In certain embodiments, at least two of the latter factors are included. In further embodiments, at least three of the latter factors are included.

In another embodiment, the expanded HSCs retain at least some of the pluripotency of the initial stem cells or HSCs. Pluripotency includes stem cell activity or potential, such as the ability to differentiate into other blood cell types or the ability to multiply without differentiating.

In another embodiment, the methods for promoting the expansion of hematopoietic stem cells further comprises the step of selecting cells after culture (e.g., cultured cells) that express at least one positive cell surface marker selected from the group consisting of Sca-1$^+$, IGF2-hFC$^+$, CD31$^+$, and Kit$^+$ and/or do not express at least one negative cell surface marker selected from the group consisting of PrP, Lin, and CD62L. In another aspect, the cultured cells express at least two positive cell surface markers and do not express at least two negative cell surface markers. In another aspect, the cultured cells express at least three positive cell surface markers and do not express at least three negative cell surface markers.

In another embodiment, the cultured cells express Sca-1+, IGF2-hFC+, CD31+ and Kit+ and do not express PrP, Lin, and CD62L. In another embodiment, the cultured cells express Sca-1+ and IGF2-hFC+ and do not express PrP, Lin, and CD62L. In still another embodiment, the method for promoting the expansion of hematopoietic stem cells comprises the step of selecting cells after culture which specifically bind to an angiopoietin-like protein.

An embodiment of the invention provides methods for promoting the expansion of hematopoietic stem cells in an individual in need of an expanded number of hematopoietic cells, comprising administering to the individual an angiopoietin-like protein in an amount effective to promote expansion of hematopoietic stem cells, thereby promoting expansion of hematopoietic cells in the individual. In an embodiment for promoting the expansion of hematopoietic stem cells in an individual, administration is by infusion.

In an embodiment, the individual is in need of expanded numbers of hematopoietic cells due to the presence of a condition including but not limited to reduced hematopoietic function, reduced immune function, reduced neutrophil count, reduced neutrophil mobilization, mobilization of peripheral blood progenitor cells, sepsis, severe chronic neutropenia, bone marrow transplants, infectious diseases, leucopenia, thrombocytopenia, anemia, enhancing engraftment of bone marrow during transplantation, enhancing bone marrow recovery in treatment of radiation, chemical or chemotherapeutic induced bone marrow aplasia or myelosuppression, and acquired immune deficiency syndrome.

The present invention also provides methods of enhancing hematopoietic recovery in a mammal that has undergone chemotherapy, comprising administering to the mammal an amount of an angiopoietin-like protein effective to promote expansion of hematopoietic stem cells in the mammal, thereby enhancing the hematopoietic recovery in the mammal that has undergone chemotherapy.

The present invention is drawn to methods of administering hematopoietic stem cells to an individual. In an embodiment, the method comprises obtaining hematopoietic stem cells from the individual or from a donor, culturing the cells in a culture medium comprising an angiopoietin-like protein, and transplanting the cultured cells into the individual.

The present invention also provides methods of treating an individual in need of a hematopoietic stem cell-based therapy, comprising removing hematopoietic stem cells from the individual or from a donor; culturing the cells in a culture medium containing an amount of an angiopoietin-like protein effective to promote expansion of hematopoietic stem cells, harvesting the cultured cells, and transplanting the cultured cells into the individual.

The present invention also provides methods of gene delivery and expression in an individual, comprising removing hematopoietic stem cells from the individual or from a donor, culturing the cells in a culture medium containing an amount of an angiopoietin-like protein effective to promote expansion of hematopoietic stem cells, introducing DNA into the cultured cells, harvesting the cultured cells, and transplanting the cultured cells into the individual.

Another embodiment of the invention provides methods for screening for a receptor for an angiopoietin-like protein, comprising screening a library of candidate proteins or a library of genes encoding candidate proteins to identify proteins which bind to the angiopoietin-like protein and/or promote the expansion of hematopoietic stem cells in culture, wherein a candidate protein that binds to angiopoietin-like protein is indicative of a receptor for angiopoietin-like protein.

The present invention also provides methods of identifying hematopoietic stem cells. In an embodiment, the method comprises screening for cells which bind to at least one angiopoietin-like protein. In another embodiment, the screening for hematopoietic stem cells further comprises selecting cells expressing at least one positive cell surface marker and/or not expressing at least one negative cell surface marker as described above.

The present invention also includes kits for identifying hematopoietic stem cells. The kit includes at least one detectably labeled angiopoietin-like protein. The angiopoietin-like protein can be labeled with any suitable detectable label such as an epitope, a fluorescent dye, or a radioactive label. Suitable epitopes include FLAG tags, myc tags and other epitopes for which specific antibodies can be made or are available. Suitable fluorescent dyes include, for example, fluorescein, rhodamine, Cy3, and Cy5. Suitable radiolabels include, for example, $^{125}$I, $^{32}$P, and $^{35}$S. Methods for using detectable labels such as epitope tags, fluorescent dyes, and radiolabels are well known in the art.

Kits for propagating hematopoietic stem cells ex vivo (e.g., in vitro) are also provided. The kit can comprise medium suitable for culturing HSCs, one or more angiopoietin-like proteins, and optionally includes instructions for expanding hematopoietic stem cells in vitro.

The various embodiments described herein can be complimentary and can be combined or used together in a manner understood by the skilled person in view of the teachings contained herein.

BRIEF DESCRIPTION OF FIGURES

FIG. 3B top panel shows representative FACS plots of peripheral blood mononuclear cells from one mouse at 9 months post-transplant (cells from bar 15 of FIG. 3A) (the number in each quadrant is the percentage of cells in each quadrant); the bottom panel shows the summary of data from all mice in bars 13 and 15 of FIG. 3A.

FIG. 3C top panel shows representative FACS plots of peripheral blood mononuclear cells from one mouse at 4 months after a secondary transplantation; the bottom panel shows the summary of data from all mice at 4 months after a secondary transplantation of mouse bone marrow represented in bars 8 and 10 of FIG. 3A.

FIG. 15 shows the amino acid sequences for exemplary angiopoietin-like proteins.

DETAILED DESCRIPTION

As described herein, freshly isolated HSCs as well as cultured HSCs bind to angiopoietin-like proteins. In addition, as described herein, angiopoietin-like proteins promote the expansion of hematopoietic stem cells. The present invention is directed to hematopoietic stem cells, methods for propagating or expanding hematopoietic stem cells, and methods of using the propagated hematopoietic stem cells.

Ex Vivo Cultures of Hematopoietic Stem Cells

Figure 14:
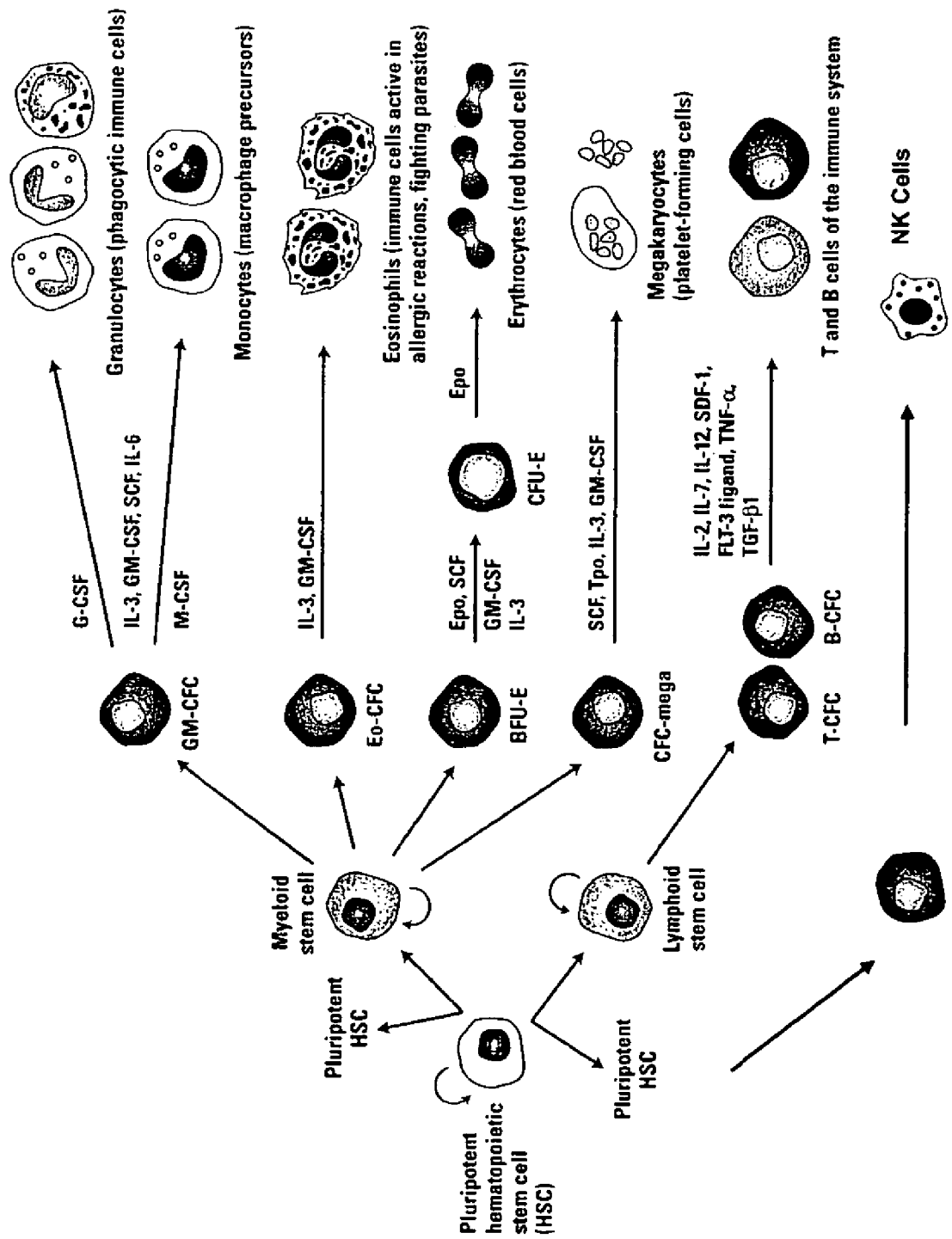
FIG. 14 is a schematic diagram of hematopoietic stem cell self renewal and differentiation into different blood cell types.

The present invention provides methods for promoting the expansion of hematopoietic stem cells (HSCs) in culture (e.g., in vitro or ex vivo). The cell or cells to be cultured can include any cell that is capable of differentiating into one or more blood cell types. Exemplary blood cell types are shown in FIG. 14 and include phagocytic immune cells (e.g., granulocytes), monocytes (e.g., macrophage precursor cells), macrophages, eosiniphils, erythrocytes, platelet forming cells (e.g., megakaryocytes), T lymphocytes, B lymphocytes, and natural killer (NK) cells. Suitable cell(s) can also be capable of self renewal, that is, capable of propagating or increasing in number and remaining at the same developmental stage as the parent cell.

Suitable cell(s) can be isolated, for example, from any known source of hematopoietic stem cells, including, but not limited to, bone marrow, mobilized peripheral blood (MPB), fetal liver, and umbilical cord blood. Umbilical cord blood is discussed, for instance, in Issaragrishi et al., N. Engl. J. Med. 332:367-369 (1995). Bone marrow cells can be obtained from a source of bone marrow, including but not limited to, ilium (e.g., from the hip bone via the iliac crest), tibia, femora, vertebrate, or other bone cavities. Other sources of stem cells include, but are not limited to, ES cells, embryonic yolk sac, fetal liver, and fetal spleen.

The cell or cells can be subjected to methods of further enrichment for hematopoietic stem cells. Means for isolating hematopoietic stem cells using specific stem cell markers are known to those skilled in the art.

The one or more cells and the hematopoietic cells of the invention can be derived from any suitable animal, e.g., human, non-human primates, porcine or murine. In one preferred embodiment, the cells are human cells.

For isolation of bone marrow, an appropriate solution can be used to flush the bone, including, but not limited to, salt solution, optionally supplemented with fetal calf serum (FCS) or other naturally occurring factors, in conjunction with an acceptable buffer. In an embodiment, the buffer is at low concentration, generally from about 5 to about 25 mM. Convenient buffers include, but are not limited to, HEPES, phosphate buffers and lactate buffers. Bone marrow can also be aspirated from the bone in accordance with conventional techniques.

Regarding lineage specific markers, the absence or low expression of lineage specific markers can be identified by the lack of binding of antibodies specific to the lineage specific markers, useful in so-called "negative selection". The source of cells for use in the methods of the present invention can be subjected to negative selection techniques to remove those cells that express lineage specific markers and retain those cells which are lineage negative ("Lin$^-$"). Lin$^-$ generally refers to cells which lack markers such as those associated with T cells (such as CD2, 3, 4 and 8), B cells (such as B220, CD48, CD10, 19 and 20), myeloid cells (such as Mac-1, Gr-1, CD14, 15, 16 and 33), natural killer ("NK") cells (such as CD244, CD2, 16 and 56), RBC (such as Ter119, and glycophorin A), megakaryocytes (CD41), mast cells, eosinophils or basophils. Methods of negative selection are known in the art. Lineage specific markers also include CD38, HLA-DR and CD71. As used herein, "Lin$^-$" refers to a cell population selected based on the lack of expression of at least one lineage specific marker.

Various techniques can be employed to separate the cells-by initially removing cells of dedicated lineage or having a particular phenotype. Monoclonal antibodies are particularly useful for identifying markers associated with particular cell lineages, stages of differentiation, or particular phenotypes. The antibodies can be attached to a solid support to allow for crude separation. The separation techniques employed should maximize the retention of viable cells in the fraction to be collected. Various techniques of different efficacy can be employed to obtain "relatively crude" separations. Such separations are up to 10%, usually not more than about 5%, of the total cells present not having the marker can remain with the cell population to be retained. In certain embodiments, not more than about 1% of the total cells present in the population of retained cells do not have the marker. The particular technique employed will depend upon efficiency of separation, associated cytotoxicity, ease and speed of performance, and necessity for sophisticated equipment and/or technical skill.

Procedures for separation can include, but are not limited to, physical separation, magnetic separation, using antibody-coated magnetic beads, affinity chromatography, cytotoxic agents joined to a monoclonal antibody or used in conjunction with a monoclonal antibody, including, but not limited to, complement and cytotoxins, and "panning" with antibody attached to a solid matrix, e.g., plate, elutriation or any other convenient technique. In certain embodiments, one uses a high throughput technique to rapidly screen and separate different cells.

The use of physical separation techniques include, but are not limited to, those based on differences in physical (density gradient centrifugation and counter-flow centrifugal elutriation), cell surface (lectin and antibody affinity), and vital staining properties (mitochondria-binding dye rho123 and DNA-binding dye Hoechst 33342). These procedures are well known to those of skill in this art.

Techniques providing accurate and rapid separation include, but are not limited to, flow cytometry (e.g., fluorescence activated cell sorting), which can have varying degrees of sophistication, e.g., a plurality of color channels, low angle and obtuse light scattering detecting channels, impedance channels, etc. Cells also can be selected by flow cytometry based on light scatter characteristics, where stem cells are selected based on low side scatter and low to medium forward scatter profiles. Cytospin preparations show the enriched stem cells to have a size between mature lymphoid cells and mature granulocytes.

For example, in a first separation step, anti-CD34 can be labeled with a first fluorochrome, while the antibodies for the various dedicated lineages, can be conjugated to a fluorochrome with different and distinguishable spectral characteristics from the first fluorochrome. While each of the lineages can be separated in more than one "separation" step, desirably the lineages are separated at the same time as one is positively selecting for HSCs. The cells can be selected and isolated from dead cells, by employing dyes associated with dead cells (including but not limited to, propidium iodide (PI)). The particular order of separation is not critical to this invention.

The cells obtained as described above can be used immediately or frozen at liquid nitrogen temperatures and stored for long periods of time, being thawed and capable of being reused. Once thawed, the cells can be expanded by use of the methods described herein.

HSCs can be expanded by culturing one or more cells in an expansion container and in a volume of a suitable medium. Cells populations highly enriched in stem cells and methods for obtaining them are described in WO 95/05843; WO 95/03693 and WO 95/08105. In a preferred embodiment the one or more cells comprises a population of cells that is substantially enriched in hematopoietic stem cells. In another embodiment, the population of cells is substantially free of stromal cells.

The cells can be cultured such that the culture well contains about 1-100 cells per well. Where the population of cells is bone marrow, the cells can be cultured at a density of about $1 \times 10^2$ cells to about $1 \times 10^7$ cells/mL of medium. In another embodiment, the cells can be cultured at a density of about $1 \times 10^5$ cells to about $1 \times 10^6$ cells/mL of medium. In another embodiment, the population of cells comprises Side Population (SP) bone marrow cells. The SP bone marrow cells can be cultured at lower density, for example from about $1 \times 10^2$ to $5 \times 10^3$ cells/ml. In a separate aspect, the population of cells can be derived from mobilized peripheral blood. The mobilized peripheral blood cells can be cultured at a density of about 20,000 cells/mL to about 50,000 cells/mL; in another embodiment, the mobilized peripheral blood cells is cultured at a density of about 50,000 cells/mL.

Any suitable expansion container, flask, or appropriate tube such as a 12, 24 or 96 well plate, 12.5 cm$^2$ T flask or gas-permeable bag can be used in the method of this invention. Such culture containers are commercially available from Falcon, Corning or Costar. As used herein, "expansion container" also is intended to include any chamber or container for expanding cells whether or not free standing or incorporated into an expansion apparatus.

Various media can be used for the expansion of the stem cells including Dulbecco's MEM, IMDM, X-Vivo 15 (serum-depleted, Cambrex), RPMI-1640 and StemSpan (Stem Cell Technologies). In another embodiment, the cell culture medium is serum free. One serum free medium which can be used in the methods of the invention is serum free StemSpan (Stem Cell Technologies). In another embodiment, the medium is supplemented with 10 µg/ml heparin.

The media formulations for expansion of HSCs contain concentrations of one or more angiopoietin-like proteins in a range from about 0.1 ng/mL to about 500 ng/mL. In another embodiment, from about 1 ng/mL to about 100 ng/mL of one or more angiopoietin-like proteins is used. In another embodiment, from about 10 ng/ml to 50 ng/ml of one or more angiopoietin-like proteins is used. Other useful concentrations of angiopoietin-like proteins can be readily determined by one of ordinary skill in the art using the teachings contained herein.

In another aspect, in addition to the angiopoietin-like protein of the invention, the media formulations for expansion of HSCs are supplemented with cytokines, including but not limited to fibroblast growth factor (FGF) (e.g. FGF-1 or FGF-2), insulin growth factor (e.g. IGF-2, or IGF-1), thrombopoietin (TPO), and stem cell factor (SCF). As indicated above, the concentrations of cytokines range from about 0.1 ng/mL to about 500 ng/mL. In another embodiment, from about 1 ng/mL to about 200 ng/mL of a cytokine is used. In another embodiment, from about 10 ng/ml to 100 ng/ml of a cytokine is used. In another embodiment, the cytokines for use in the invention are FGF-1,TPO, IGF-2, and SCF: In still another embodiment the SCF is present at 10 ng/ml concentration, TPO at 20 ng/ml concentration, IGF-2 at 20 ng/ml concentration and FGF-1 at 10 ng/ml concentration. Other cytokines may be added, alone or in combination, and include but are not limited to G-CSF, GM-CSF, IL-1α., and IL-11. Other useful concentrations of cytokines can be readily determined by one of ordinary skill in the art using the teachings contained herein.

Transplantation

The expanded cultured hematopoietic stem cells of the invention can be used for a variety of applications, including transplantation, sometimes referred to as cell-based therapies or cell replacement therapies, such as bone marrow transplants, gene therapies, tissue engineering, and in vitro organogenesis.

Hematopoietic progenitor cell expansion for bone marrow transplantation is a potential application of human bone marrow cultures. Human autologous and allogeneic bone marrow transplantation are currently used as therapies for diseases such as leukemia, lymphoma, and other life-threatening diseases. For these procedures, however, a large amount of donor bone marrow must be removed to ensure that there are enough cells for engraftment. The methods of the present invention circumvent this problem. Methods of transplantation are known to those skilled in the art.

Expanded hematopoietic stem cells are particularly suited for reconstituting hematopoietic cells in a subject or for providing cell populations enriched in desired hematopoietic cell types. This method involves administering by standard means, such as intravenous infusion or mucosal injection, the expanded cultured cells to a patient.

The discovery that cells may be expanded ex vivo and administered intravenously provides the means for systemic administration. For example, bone marrow-derived stem cells may be isolated with relative ease and the isolated cells may be cultured according to methods of the present invention to increase the number of cells available. Intravenous administration also affords ease, convenience and comfort at higher levels than other modes of administration. In certain applications, systemic administration by intravenous infusion is more effective overall. In another embodiment, the stem cells are administered to an individual by infusion into the superior mesenteric artery or celiac artery. The cells may also be delivered locally by irrigation down the recipient's airway or by direct injection into the mucosa of the intestine.

After isolating the cells, the cells can be cultured for a period of time sufficient to allow them to expand to desired numbers, without any loss of desired functional characteristics. For example cells can be cultured from 1 day to over a year. In another embodiment, cells are cultured for 3 to 30 days. In another embodiment, cells are cultured for 4 to 14 days. In yet another embodiment, cells can be cultured for at least 7 days.

Between $10^5$ and $10^{13}$ cells per 100 kg person are administered per infusion. In another embodiment, about $1 \times 10^8$ to about $5 \times 10^{12}$ cells are infused intravenously per 100 kg person. In another embodiment, between about $1 \times 10^9$ and $5 \times 10^{11}$ cells are infused intravenously per 100 kg person. For example, dosages such as $4 \times 10^9$ cells per 100 kg person and $2 \times 10^{11}$ cells can be infused per 100 kg person.

In some embodiments, a single administration of cells is provided. In other embodiments, multiple administrations are used. Multiple administrations can be provided over periodic time periods such as an initial treatment regime of 3 to 7 consecutive days, and then repeated at other times.

With respect to cells as administered to a patient, an effective amount may range from as few as several hundred or fewer to as many as several million or more. In specific embodiments, an effective amount may range from $10^3$ to $10^8$. It will be appreciated that the number of cells to be administered will vary depending on the specifics of the disorder to be treated, including but not limited to size or total volume/surface area to be treated, as well as proximity of the site of administration to the location of the region to be treated, among other factors familiar to the medicinal biologist.

The terms effective period (or time) and effective conditions refer to a period of time or other controllable conditions (e.g., temperature, humidity for in vitro methods), necessary or preferred for an agent or pharmaceutical composition to achieve its intended result.

The term pharmaceutically acceptable carrier (or medium), which may be used interchangeably with the term biologically compatible carrier or medium, refers to reagents, cells, compounds, materials, compositions, and/or dosage forms which are, within the scope of sound medical judgment, suitable for use in contact with the tissues of human beings and animals without excessive toxicity, irritation, allergic response, or other complication commensurate with a reasonable benefit/risk ratio. As described in greater detail herein, pharmaceutically acceptable carriers suitable for use in the present invention include liquids, semi-solid (e.g., gels) and solid materials (e.g., cell scaffolds). As used herein, the term biodegradable describes the ability of a material to be broken down (e.g., degraded, eroded, dissolved) in vivo. The term includes degradation in vivo with or without elimination (e.g., by resorption) from the body. The semi-solid and solid materials may be designed to resist degradation within the body (non-biodegradable) or they may be designed to degrade within the body (biodegradable, bioerodable). A biodegradable material may further be bioresorbable or bioabsorbable, e.g., it may be dissolved and absorbed into bodily fluids (water-soluble implants are one example), or degraded and ultimately eliminated from the body, either by conversion into other materials or by breakdown and elimination through natural pathways.

Several terms are used herein with respect to transplantation therapies, also known as cell-based therapies or cell replacement therapy. The terms autologous transfer, autologous transplantation, autograft and the like refer to treatments wherein the cell donor is also the recipient of the cell replacement therapy. The terms allogeneic transfer, allogeneic transplantation, allograft and the like refer to treatments wherein the cell donor is of the same species as the recipient of the cell replacement therapy, but is not the same individual. A cell transfer in which the donor's cells have been histocompatibly matched with a recipient is sometimes referred to as a syngeneic transfer. The terms xenogeneic transfer, xenogeneic transplantation, xenograft and the like refer to treatments wherein the cell donor is of a different species than the recipient of the cell replacement therapy.

The expanded hematopoietic cells can be used for reconstituting the full range of hematopoietic cells in an immunocompromised host following therapies such as, but not limited to, radiation treatment and chemotherapy. Such therapies destroy hematopoietic cells either intentionally or as a side-effect of bone marrow transplantation or the treatment of lymphomas, leukemias and other neoplastic conditions, e.g., breast cancer.

Expanded hematopoietic cells are also useful as a source of cells for specific hematopoietic lineages. The maturation, proliferation and differentiation of expanded hematopoietic cells into one or more selected lineages may be effected through culturing the cells with appropriate factors including, but not limited to, erythropoietin (EPO), colony stimulating factors, e.g., GM-CSF, G-CSF, or M-CSF, SCF, interleukins, e.g., IL-1, -2, -3, -4, -5, -6, -7, -8, -13, etc., or with stromal cells or other cells which secrete factors responsible for stem cell regeneration, commitment, and differentiation.

Drug Discovery

Expanded hematopoietic cells of the invention are useful for identifying culture conditions or biological modifiers such as growth factors which promote or inhibit such biological responses of stem cells as self-regeneration, proliferation, commitment, differentiation, and maturation. In this way one may also identify, for example, receptors for these biological modifiers, agents which interfere with the interaction of a biological modifier and its receptor, and polypeptides, antisense polynucleotides, small molecules, or environmental stimuli affecting gene transcription or translation.

For example, the present invention makes it possible to prepare relatively large numbers of hematopoietic stem cells for use in assays for the differentiation of stem cells into various hematopoietic lineages. These assays may be readily adapted in order to identify substances such as factors which, for example, promote or inhibit stem cell self-regeneration, commitment, or differentiation.

The invention provides methods to identify receptors for the angiopoietin-like proteins. Receptors for these orphan ligands have not yet been identified.

Accordingly, the invention provides methods for screening for a receptor for an angiopoietin-like protein, comprising screening a library of candidate proteins or a library of genes encoding candidate proteins to identify proteins which bind to the angiopoietin-like protein and/or promote the expansion of hematopoietic stem cells in culture. In an embodiment, a library of candidate genes is introduced into and expressed in cells that do not normally bind to the angiopoietin-like protein of interest. These cells can then be exposed to one or more angiopoietin-like proteins. Cells that bind to the angiopoietin-like protein and/or expand upon exposure to the angiopoietin-like protein are indicative of cells that contain an angiopoietin-like protein receptor. The cells that bind or expand in the presence of the angiopoietin-like protein can be isolated, and the transfected gene can be isolated from the cells.

Gene Cloning Strategies

One may also use the expanded cells of the invention to identify and clone genes whose expression is associated with proliferation, commitment, differentiation, and maturation of stem cells or other hematopoietic cells, e.g., by subtractive hybridization or by expression cloning using monoclonal antibodies specific for target antigens associated with these biological events or characteristic of a hematopoietic cell type.

Gene Delivery and Expression

As described above hematopoietic stem cells are also important targets for gene delivery and expression in a subject. One such embodiment is sometimes referred to as gene therapy.

According to the invention, the cultured expanded cells can be further genetically altered prior to reintroducing the cells into an individual for gene therapy, to introduce a gene whose expression has therapeutic effect on the individual. Methods for introducing genes into the cultured cells are provided in detail below.

In some aspects of the invention, individuals can be treated by supplementing, augmenting and/or replacing defective and/or damaged cells with cells that express a therapeutic gene. The cells may be derived from cells of a normal matched donor or stem cells from the individual to be treated (i.e., autologous). By introducing normal genes in expressible form, individuals suffering from such a deficiency can be provided the means to compensate for genetic defects and eliminate, alleviate or reduce some or all of the symptoms.

Expression vectors may be introduced into and expressed in autologous or allogeneic expanded hematopoietic cells, or the genome of cells may be modified by homologous or non-homologous recombination by methods known in the art. In this way, one may correct genetic defects in an individual or provide genetic capabilities naturally lacking in stem cells. For example, diseases including, but not limited to, β-thalassemia, sickle cell anemia, adenosine deaminase deficiency, recombinase deficiency, and recombinase regulatory gene deficiency may be corrected in this fashion. Diseases not associated with hematopoietic cells may also be treated, e.g., diseases related to the lack of secreted proteins including, but not limited to hormones, enzymes, and growth factors. Inducible expression of a gene of interest under the control of an appropriate regulatory initiation region will allow production (and secretion) of the protein in a fashion similar to that in the cell which normally produces the protein in nature.

Similarly, one may express in expanded hematopoietic cells a ribozyme, antisense RNA or protein to inhibit the expression or activity of a particular gene product. Drug resistance genes including, but not limited to, the multiple drug resistance (MDR) gene, may also be introduced into cells, e.g., to enable them to survive drug therapy. For hematotrophic pathogens, such as HIV or HTLV-I, and HTLV II, the cells can be genetically modified to produce an antisense RNA, ribozyme, or protein which would prevent the proliferation of a pathogen in hematopoietic stem cells or differentiated cells arising from the stem cells. One may also disable or modulate the expression of a particular genetic sequence by methods known in the art, including, but not limited to, directly substituting, deleting, or adding DNA by homologous recombination or indirectly by antisense sequences.

Transduction of Hematopoietic Stem Cell Cultures

The expanded hematopoietic stem cells of the invention can be genetically modified. The introduction of the gene into the hematopoietic stem cell can be by standard techniques, e.g. infection, transfection, transduction or transformation. Examples of modes of gene transfer include e.g., naked DNA, $CaPO_4$ precipitation, DEAE dextran, electroporation, protoplast fusion, lipofection, cell microinjection, and viral vectors, adjuvant-assisted DNA, gene gun, catheters, etc. In another embodiment, a viral vector is used.

Polynucleotides are inserted into vector genomes using methods well known in the art. For example, insert and vector DNA can be contacted, under suitable conditions, with a restriction enzyme to create complementary ends on each molecule that can pair with each other and be joined together with a ligase. Alternatively, synthetic nucleic acid linkers can be ligated to the termini of restricted polynucleotide. These synthetic linkers contain nucleic acid sequences that correspond to a particular restriction site in the vector DNA. Additionally, an oligonucleotide containing a termination codon and an appropriate restriction site can be ligated for insertion into a vector containing, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; versatile multiple cloning sites; and T7 and SP6 RNA promoters for in vitro transcription of sense and antisense RNA. Other means are well known and available in the art.

Modification of hematopoietic stem cells can comprise the use of an expression cassette created for either constitutive or inducible expression of the introduced transgene. Such an expression cassette can include regulatory elements such as a promoter, an initiation codon, a stop codon, and a polyadenylation signal. It is necessary that these elements be operable in the stem cells or in cells that arise from the stem cells after infusion into an individual. Moreover, it is necessary that these elements be operably linked to the nucleotide sequence that encodes the protein such that the nucleotide sequence can be expressed in the stem cells and thus the protein can be produced. Initiation codons and stop codons are generally considered to be part of a nucleotide sequence that encodes the protein.

A variety of promoters can be used for expression of the transgene. Promoters that can be used to express the gene are well known in the art. Promoters include cytomegalovirus (CMV) intermediate early promoter, a viral LTR such as the Rous sarcoma virus LTR, HIV-LTR, HTLV-1 LTR, the simian virus 40 (SV40) early promoter, *E. coli* lac UV5 promoter and the herpes simplex tk virus promoter. For example, one can use a tissue specific promoter, i.e. a promoter that functions in some tissues but not in others. Such promoters include EF2 responsive promoters, etc. Examples of promoters that may be used to cause expression of the introduced sequence in specific cell types include Granzyme A for expression in T-cells and NK cells, the CD34 promoter for expression in stem and progenitor cells, the CD8 promoter for expression in cytotoxic T-cells, and the CD11b promoter for expression in myeloid cells.

Regulatable promoters can be used. Such systems include those using the lac repressor from *E. coli* as a transcription modulator to regulate transcription from lac operator-bearing mammalian cell promoters (Brown, M. et al., *Cell*, 49:603-612 (1987)), those using the tetracycline repressor (tetR) (Gossen, M., and Bujard, H., *Proc. Natl. Acad. Sci. USA* 89:5547-5551 (1992); Yao, F. et al., *Human Gene Therapy*, 9:1939-1950 (1998); Shockelt, P., et al., *Proc. Natl. Acad. Sci. USA*, 92:6522-6526 (1995)). Other systems include FK506 dimer, VP16 or p65 using astradiol, RU486, diphenol murislerone or rapamycin. Inducible systems are available from Invitrogen, Clontech and Ariad. Systems using a repressor with the operon can be used in the invention. Regulation of transgene expression in target cells represents a critical aspect of gene therapy. For example, the lac repressor from *Escherichia coli* can function as a transcriptional modulator to regulate transcription from lac operator-bearing mammalian cell promoters (M. Brown et al., *Cell*, 49:603-612 (1987); Gossen and Bujard (1992); M. Gossen et al., *Natl. Acad. Sci. USA*, 89:5547-5551 (1992)) combined the tetracycline repressor (tetR) with the transcription activator (VP16) to create a tetR-mammalian cell transcription activator fusion protein, tTa (tetR-VP16), with the teto-bearing minimal promoter derived from the human cytomegalovirus (hCMV) major immediate-early promoter to create a tetR-tet operator system to control gene expression in mammalian cells. Yao and colleagues (F. Yao et al., *Human Gene Therapy*, supra) demonstrated that the tetracycline repressor (tetR) alone, rather than the tetR-mammalian cell transcription factor fusion derivatives can function as potent trans-modulator to regulate gene expression in mammalian cells when the tetracycline operator is properly positioned downstream for the TATA element of the CMVIE promoter. One particular advantage of this tetracycline inducible switch is that it does not require the use of a tetracycline repressor—mammalian cells transactivator or repressor fusion protein, which in some instances can be toxic to cells (M. Gossen et al., *Natl. Acad. Sci. USA*, 89:5547-5551 (1992); P. Shockett et al., *Proc. Natl. Acad. Sci. USA*, 92:6522-6526 (1995)), to achieve its regulatable effects.

The effectiveness of some inducible promoters increases over time. In such cases one can enhance the effectiveness of such systems by inserting multiple repressors in tandem, e.g. TetR linked to a TetR by an IRES. Alternatively, one can wait at least 3 days before screening for the desired function. While some silencing may occur, it is minimized given the large number of cells being used, for example if at least $1 \times 10^4$ to about $1 \times 10^7$ cells are used, the effect of silencing is minimal. One can enhance expression of desired proteins by known means to enhance the effectiveness of this system. For example, using the Woodchuck Hepatitis Virus Posttranscriptional Regulatory Element (WPRE). See Loeb, V. E., et al., *Human Gene Therapy* 10:2295-2305 (1999); Zufferey, R., et al., *J. of Virol.* 73:2886-2892 (1999); Donello, J. E., et al., *J. of Virol.* 72:5085-5092 (1998).

Examples of polyadenylation signals useful to practice the present invention include but are not limited to human collagen I polyadenylation signal, human collagen II polyadenylation signal, and SV40 polyadenylation signal.

The exogenous genetic material that includes the transgene operably linked to the regulatory elements may remain present in the cell as a functioning cytoplasmic molecule, a functioning episomal molecule or it may integrate into the cell's chromosomal DNA. Exogenous genetic material may be introduced into cells where it remains as separate genetic material in the form of a plasmid. Alternatively, linear DNA, which can integrate into the chromosome, may be introduced into the cell. When introducing DNA into the cell, reagents, which promote DNA integration into chromosomes, may be added. DNA sequences, which are useful to promote integration, may also be included in the DNA molecule. Alternatively, RNA may be introduced into the cell.

Selectable markers can be used to monitor uptake of the desired gene into the hematopoietic stem cells of the invention. These marker genes can be under the control of any promoter or an inducible promoter. These are well known in the art and include genes that change the sensitivity of a cell to a stimulus such as a nutrient, an antibiotic, etc. Genes include those for neo, puro, and tk, multiple drug resistance (MDR), etc. Other genes express proteins that can readily be screened for such as green fluorescent protein (GFP), blue fluorescent protein (BFP), luciferase, and LacZ.

The HSC cells can be transduced with a therapeutic gene. For example, the transduction can be via a viral vector such as a retroviral vector (e.g. as described in for example, WO 94/29438, WO 97/21824 and WO 97/21825) or a pox viral vector. When transduction is ex vivo, the transduced cells are subsequently administered to the recipient. Thus, the invention encompasses treatment of diseases amenable to gene transfer into HSCs, by administering the gene ex vivo or in vivo by the methods disclosed herein. For example, diseases including, but not limited to, β thalassemia, sickle cell anemia, adenosine deaminase deficiency, recombinase deficiency, recombinase regulatory gene deficiency, etc. can be corrected by introduction of a therapeutic gene. Other indications of gene therapy are introduction of drug resistance genes to enable normal stem cells to have an advantage and be subject to selective pressure during chemotherapy. Suitable drug resistance genes include, but are not limited to, the gene encoding the multidrug resistance (MDR) protein.

Diseases other than those associated with hematopoietic cells can also be treated by genetic modification, where the disease is related to the lack of a particular secreted product including, but not limited to, hormones, enzymes, interferons, growth factors, or the like. By employing an appropriate regulatory initiation region, inducible production of the deficient protein can be achieved, so that production of the protein will parallel natural production, even though production will be in a different cell type. from the cell type that normally produces such protein. It is also possible to insert a ribozyme, antisense or other message to inhibit particular gene products or susceptibility to diseases, particularly hematolymphotropic diseases.

As used herein, therapeutic gene can be an entire gene or only the functionally active fragment of the gene capable of compensating for the deficiency in the patient that arises from the defective endogenous gene. Therapeutic gene also encompasses antisense oligonucleotides or genes useful for antisense suppression and ribozymes for ribozyme-mediated therapy. Therapeutic genes that encode dominant inhibitory oligonucleotides and peptides as well as genes that encode regulatory proteins and oligonucleotides also are encompassed by this invention. Generally, gene therapy will involve the transfer of a single therapeutic gene although more than one gene may be necessary for the treatment of particular diseases. The therapeutic gene can be a normal, i.e. wild-type, copy of the defective gene or a functional homolog. In a separate embodiment, the therapeutic gene is a dominant inhibiting mutant of the wild-type. More than one gene can be administered per vector or alternatively, more than one gene can be delivered using several compatible vectors. Depending on the genetic defect, the therapeutic gene can include the regulatory and untranslated sequences. For gene therapy in human patients, the therapeutic gene will generally be of human origin although genes from other closely related species that exhibit high homology and biologically identical or equivalent function in humans may be used, if the gene product does not induce an adverse immune reaction in the recipient. For example, a primate insulin gene whose gene product is capable of converting glucose to glycogen in humans would be considered a functional equivalent of the human gene. The therapeutic gene suitable for use in treatment will vary with the disease. For example, a suitable therapeutic gene for treating sickle cell anemia is a normal copy of the globin gene. A suitable therapeutic gene for treating SCID is the normal ADA gene.

General Considerations

For each of the embodiments described herein, a number of variations can be made as described below, without departing from the scope of the invention.

The term "about" in the context of numerical values and ranges refers to values or ranges that approximate or are close to the recited values or ranges such that the invention can perform as intended, such as having a desired rate, amount, degree or extent of stem cell activity, as is apparent from the teachings contained herein. Thus, this term encompasses values beyond those simply resulting from systematic error.

Angiopoietin-like protein (Angptl) can be any member of a family of secreted glycosylated proteins that are similar in structure to angiopoietins (Oike et al., Int. J. Hematol. 80:21-8 (2004)). Similar to angiopoietins, angiopoietin-like proteins contain an N-terminal coiled-coil domain and a C-terminal fibrinogen-like domain. Unlike angiopoietins, angiopoietin-like proteins do not bind to the tyrosine kinase receptor Tie2. Angiopoietin-like proteins include angiopoietin-like proteins 2, 3, 4, 5, 6, and 7. Angiopoietin-like proteins also include microfibrillar-associated glycoprotein 4 (Mfap4), and analogs and equivalents thereof. Angptl2 has been described by Kim, I. et al. J Biol Chem 274, 26523-8 (1999)). In addition, angiopoietin-like proteins are available commercially (R&D Systems, Abnova Corp). Angiopoietin-like proteins 2, 3, 4, 5, 7, and Mfap4 are preferred.

Exemplary angiopoietin-like proteins are provided, for example in GenBank as Accession Number AAH12368 (human Angptl2 precursor; SEQ ID NO: 3) Accession Number AAH58287 (human Angptl3 precursor; SEQ ID NO: 4) Accession Number AAH23647 (human Angptl4; SEQ ID NO: 5) and Accession Number AAH49170 (human Angptl5; SEQ ID NO: 6). SEQ ID NOs: 3 through 6 are shown in FIG. 15. Other suitable angiopoietin-like proteins share at least 60% sequence homology with any one of SEQ ID NOs: 4 to 6. In other embodiments, suitable angiopoietin-like proteins share at least 70% or at least 80% or at least 90% sequence homology with SEQ ID NOs: 4 to 6. An exemplary sequence for Angptl7 is found in GenBank Accession No. AAH01881. An exemplary sequence for Mfap4 is found in GenBank Accession No. NP_002395. The exemplary sequences of Angptl proteins having the GenBank Accession Nos. provided above are hereby incorporated by reference. In addition to naturally-occurring Angptl sequences, the skilled artisan will further appreciate that suitable Angptl proteins include those proteins that have changes in the naturally occurring amino acid sequence wherein the altered Angptl sequence retains functional ability of the Angptl protein. Suitable alterations include changes to or elimination of non-essential amino acid residues as well as conservative amino acid changes (e.g., replacing an amino acid residue with an amino acid residue having a similar side chain).

Suitable equivalents for angiopoietin-like protein include proteins and polypeptides having similar biological activity to these factors as wild-type or purified angiopoietin-like proteins (e.g., recombinantly produced). Suitable analogs of angiopoietin-like proteins include fragments retaining the desired activity and related molecules. One preferred analog is a fragment of the angiopoietin-like protein containing the coiled coil domain. For example, the coiled coil domain of angiopoietin-like protein 2. As shown herein, the coiled coil domain stimulates HSC expansion. Another analog is the fibrinogen-like domain. Fragments of Angptls such as the coiled-coil domain and the fibrinogen-like domain may be easier to express and to purify compared to full-length protein. Molecules capable of binding the corresponding angiopoietin-like protein receptor and initiating one or more biological actions associated with angiopoietin-like protein binding to its receptor are also within the scope of the invention.

The angiopoietin-like protein can be naturally produced or can be produced by expressing a gene encoding the angiopoietin-like protein in a suitable host using any suitable expression method. The host can be, for example, bacteria, yeast, or cell culture. The cell culture can be, for example, insect cell culture, or mammalian cell culture. The angiopoietin-like protein can be glycosylated. In another embodiment, the angiopoietin-like protein is glycosylated in the same or substantially the same manner as the naturally occurring angiopoietin-like protein.

As described herein, hematopoietic stem cells have the ability to differentiate into any of several types of blood cells, including red blood cells, white blood cells, including lymphoid cells and myeloid cells. As described herein, HSCs include hematopoietic cells having long-term engrafting potential in vivo. Long term engrafting potential (e.g., long term hematopoietic stem cells) can be determined using animal models or in vitro models.

Animal models for long-term engrafting potential of candidate human hematopoietic stem cell populations include the non-obese diabetic/severe combined immunodeficiency mouse (NOD/SCID) model, the SCID-hu bone model (Kyoizumi et al. (1992) Blood 79:1704; Murray et al. (1995) Blood 85(2) 368-378) and the in utero sheep model (Zanjani et al. (1992) J. Clin. Invest. 89:1179). For a review of animal models of human hematopoiesis, see Srour et al. (1992) J. Hematother. 1:143-153 and the references cited therein. An in vitro model for stem cells is the long-term culture-initiating cell (LTCIC) assay, based on a limiting dilution analysis of the number of clonogenic cells produced in a stromal co-culture after 5 to 8 weeks (Sutherland et al. (1990) Proc. Nat'l Acad. Sci. 87:3584-3588). The LTCIC assay has been shown to correlate with another commonly used stem cell assay, the cobblestone area forming cell (CAFC) assay, and with long-term engrafting potential in vivo (Breems et al. (1994) Leukemia 8:1095).

As used herein, expansion or propagation includes any increase in cell number. Expansion includes, for example, an increase in the number of hematopoietic stem cells over the number of HSCs present in the cell population used to initiate the culture. Expansion can also include increased survival of existing cells, such as hematopoietic stem cells. The term survival refers to the ability to continue to remain alive or function.

The cell or cells used to inoculate the cell culture may be derived from any source including bone marrow, both adult and fetal, cytokine or chemotherapy mobilized peripheral blood, fetal liver, bone marrow or umbilical cord blood. Isolated fractions of cells can be used. For example, a purified "side population" (SP) cells obtained from bone marrow or other sources can be used. Other enriched populations of HSCs can also be used. Methods for isolating enriched populations of HSCs are known to those in the art, e.g. methods for obtaining SP cells are described in Goodell et al., J. Exp. Med. 183, 1797-806 (Apr. 1, 1996).

Separation of stem cells from a cell population can be performed by any number of methods, including cell sorters, (e.g., fluorescence activated cell sorters) magnetic beads, and packed columns. Exemplary of a highly enriched stem cell population is a population having the $CD34^+Thy^-1^+LIN^-$ phenotype as described in U.S. Pat. No. 5,061,620. A population of this phenotype will typically have an average CAFC frequency of approximately 1/20 (Murray et al. (1995) supra; Lansdorp et al., J. Exp. Med. 177:1331 (1993)). It will be appreciated by those of skill in the art that the enrichment provided in any stem cell population will be dependent both on the selection criteria used as well as the purity achieved by the given selection techniques. Methods for isolating highly enriched populations of hematopoietic stem cells are further provided in U.S. patent application Ser. No. 5,681,559. The population of cells can be from any suitable animal. The cells can be derived from a mammal. Suitable mammals include human, non-human primate, cow, horse, dog, cat, mouse and the like. In an embodiment, the cells are human cells, in still another embodiment, the cells are murine cells.

The method of the invention can be used to stimulate the expansion of any stem cells which expand in the presence of an angiopoietin-like protein, including other types of adult stem cells such as endothelial progenitor cells (Shi, Q. et al. (1998), Blood. 92, 362-367), bone marrow stromal stem cells (Owen, M. (1988), J. Cell Science Supp. 10, 63-76), mesenchymal stem cells (Pittenger, M. F. and Marshak, D. R. (2001), Marshak, D. R., Gardner, D. K., and Gottlieb, D. eds. Cold Spring Harbor, N.Y.: Cold Spring Harbor Laboratory Press 349-374), and skeletal muscle stem cells (Gussoni, E., et al. (1999), Nature. 401, 390-394), embryonic stem cells, as well as others. In another embodiment, the stem cells are endothelial progenitor cells, which are believed to share the same precursor—hemangioblasts—as HSCs.

As used herein, the term cytokine refers to any one of the numerous factors that exert a variety of effects on cells, for example, inducing growth or proliferation or preventing cell death. Non-limiting examples of additional cytokines which may be used in combination in the practice of the present invention include, interleukin-2 (IL-2), interleukin 3 (IL-3), interleukin 6 (IL-6) including soluble IL-6 receptor, interleukin 12 (IL12), G-CSF, granulocyte-macrophage colony stimulating factor (GM-CSF), interleukin 1 alpha (IL-1 α), interleukin 11 (IL-11), MIP-1 α, leukemia inhibitory factor (LIF), and flt3 ligand. The present invention also includes culture conditions in which one or more cytokine is specifically excluded from the medium. Cytokines are commercially available from several vendors such as, for example, Amgen (Thousand Oaks, Calif.), R & D Systems (Minneapolis, Minn.) and Immunex (Seattle, Wash.).

Cytokines useful to promote expansion of hematopoeitic stem cells in methods of the invention include fibroblast growth factor (FGF) (e.g. FGF-1 or FGF-2), insulin growth factor (e.g. IGF-2, or IGF-1) thrombopoietin (TPO), and stem cell factor (SCF). Accordingly, in another embodiment, the media includes at least two of FGF, IGF, TPO and SCF or analogs and equivalents thereof. Equivalents thereof include molecules having similar biological activity to these factors (i.e. FGF, TPO, IGF and SCF) as wild-type or purified cytokines (e.g., recombinantly produced). Analogs include fragments retaining the desired activity and related molecules. For example, TPO is a ligand of the mp1 receptor, thus molecules capable of binding the mp1 receptor and initiating one or more biological actions associated with TPO binding to mp1 are also within the scope of the invention. An example of a TPO mimetic is found in Cwirla et. al., Science 276:1696 (1997).

Culturing includes incubating cells in a suitable medium in vitro. It is understood that the descendants of a cell grown in culture may not be completely identical (either morphologically, genetically, or phenotypically) to the parent cell. Suitable media that can be used for culturing HSCs are known to those in the art. Illustrative media include HEPES, Dulbecco's MEM, IMDM RPMI-1640, and StemSpan (Stem Cell Technologies) that can be supplemented with a variety of different nutrients, heparin, antibiotics, growth factors, cytokines, etc. Suitable conditions comprise culturing at 33° to 39° C., and preferably around 37° C. The effect of oxygen concentration on culturing HSCs is known in the art, for example, see Cipolleschi et al. (1993), Blood 82:2031-7. HSCs can be cultured in an oxygen concentration of 1 to 10%. In another embodiment, the oxygen concentration is 1 to 5%, for example, 1% oxygen. In another embodiment, the HSCs are cultured under hypoxic conditions. Media can be replaced throughout the culture period. In another embodiment, half of the medium is replaced twice per week with fresh media. The cells can be cultured from 3 to 30 days. In another embodiment, the population of cells including HSCs is cultured for at least four weeks. in another embodiment, the population of cells including HSCs is cultured for up to two weeks. In another embodiment, the population of cells including HSCs is cultured for 7 to 14 days. In another embodiment, the population of cells including HSCs is cultured for 10 days.

An effective amount is an amount sufficient to effect beneficial or desired results: An effective amount can be administered in one or more administrations. For purposes of this invention, an effective amount of the angiopoietin-like protein and/or cytokine used herein is an amount that is sufficient to promote expansion of hematopoietic stem cells. In another embodiment, an effective amount of the various cytokines individually may be from about 0.1 ng/mL to about 500 ng/mL. In another embodiment, from about 1 ng/mL to about 200 ng/mL can be used. In another embodiment, from about 10 ng/ml to 100 ng/ml of the cytokines can be used.

An isolated or purified population of cells is substantially free of cells and materials with which it is associated in nature. For example, isolated hematopoietic stem cells comprise a population of cells that is at least 50% hematopoietic stem cells, or at least 70% hematopoietic stem cells, or at least 80% hematopoietic stem cells. In yet another embodiment, an isolated or purified population of hematopoietic stem cells comprises at least 90% hematopoietic stem cells, or is 100% hematopoietic stem cells. Substantially free of stromal cells can comprise a cell population which, when placed in a culture system as described herein, does not form an adherent cell layer.

A subject or individual is a vertebrate. In an embodiment, the individual is a mammal. Mammals include, but are not limited to, humans, non-human primates, mice, cows, horses, dogs, cats and the like. In a preferred embodiment, the mammal is a human.

The expanded hematopoietic cells of the invention can be genetically modified. As used herein, a genetic modification can include any addition, deletion or disruption to the nucleotide sequence of a cell. The methods of this invention are intended to encompass any method of gene transfer into hematopoietic stem cells, including but not limited to viral mediated gene transfer, liposome mediated transfer, transformation, transfection and transduction, e.g., viral mediated gene transfer such as the use of vectors based on DNA viruses such as adenovirus, adeno-associated virus and herpes virus, as well as retroviral based vectors. Other non limiting examples of vectors include non-viral vectors such as DNA/liposome complexes, and targeted viral protein DNA complexes. To enhance delivery of non viral vectors to a cell, the nucleic acid or proteins can be conjugated to antibodies or binding fragments thereof which bind cell surface antigens, e.g., Sca-1$^+$, IGF2-hFC$^+$, and CD31$^+$. Where freshly isolated HSCs are used, additional suitable surfaced markers include endoglin$^+$ and CD150$^+$. Liposomes that also comprise a targeting antibody or fragment thereof can be used in the methods of this invention.

As used herein, the terms transgene, heterologous gene, exogenous genetic material, exogenous gene, and nucleotide sequence encoding the gene are used interchangeably and are meant to refer to genomic DNA, cDNA, synthetic DNA and RNA, mRNA and antisense DNA and RNA which is introduced into the hematopoietic stem cell. The exogenous genetic material may be heterologous or an additional copy or copies of genetic material normally found in the individual or animal. When cells are to be used as a component of a pharmaceutical composition in a method for treating human diseases, conditions or disorders, the exogenous genetic material that is used to transform the cells may also encode proteins selected as therapeutics used to treat the individual and/or to make the cells more amenable to transplantation.

A viral vector is defined as a recombinantly produced virus or viral particle that comprises a polynucleotide to be delivered into a host cell, either in vivo, ex vivo or in vitro. Examples of viral vectors include retroviral vectors such as lentiviral vectors; adenovirus vectors; adeno-associated virus vectors and the like. In aspects where gene transfer is mediated by a retroviral vector, a vector construct refers to the polynucleotide comprising the retroviral genome or part thereof, and a therapeutic gene.

The following example is not intended to limit the present invention in any way.

EXAMPLE

Materials and Methods

Animals

C57 BL/6 CD45.2 and CD45.1 mice were purchased from the Jackson Laboratory or the National Cancer Institute and were maintained at the Whitehead Institute animal facility. All animal experiments were performed with the approval of M.I.T. Committee on Animal Care.

FACS Sorting

Donor bone marrow cells were isolated from 8 to 10 week old C57BL/6 CD45.2 mice. To sort SP Sca-1$^+$ CD45$^+$ cells, adult mouse bone marrow SP cells (stained as previously described (Zhang, C. C. & Lodish, H. F. Blood 103, 2513-21 (2004) and Zhang, C. C. & Lodish, H. F. Blood 105, 4314-20 (2005)) were further stained with anti-Sca-1-PE and anti-CD45-FITC followed by cell sorting on a MoFlo® sorter.

To sort cells that bind or that do not bind to Angptl2, 1×10$^6$ bone marrow cells were resuspended in 1 ml conditioned medium, containing ~1 µg/ml FLAG-Angptl2 or FLAG-hFc-Angptl2 as determined by Western blotting, at 4° C. for 30 min, followed by staining with APC-anti-FLAG M2 or anti-hFc IgG1-PE antibody, respectively. The conditioned medium from mock-transfected cells was used as control.

DNA Array Experiments and Analyses

Total RNA and cRNA were prepared for hybridization to Affymetrix U74Bv2 and U74Cv2 mouse chips according to the manufacturer's instructions. Briefly, total RNA was isolated with TRIzol. 15 µg of total RNA was used for first strand and second strand cDNA synthesis, followed by in vitro transcription using Ambion T7 MegaScript Kit to produce biotinylated cRNAs. Fragmented cRNAs were then hybridized to Affymetrix U74Bv2 and U74Cv2 mouse chips at 45° C. for 16 h. Arrays were washed, stained, and scanned. Microarray data was analyzed by Microarray Suite. Background elements which were not detected in the array of fetal liver CD3+ cell samples (defined as perfect match hybridization not significantly different from mismatch control signal intensity according to Microarray Suite analysis) were filtered out. An arbitrary raw value of 50 was allocated for genes whose expression levels were undetectable or whose scan readouts were below 50 in arrays of splenic CD3+ or fetal liver Gr-1+ cell samples, in order to facilitate calculation of the fold changes. Array measurements for all samples were then normalized with arrays hybridized with cRNAs prepared from the control cells by using the median of the hybridization signals of all genes. Transcripts in fetal liver CD3+ cells that had a normalized value>2.0 were selected. For each candidate transcript, its refseq nucleotide ID was retrieved from the Affymetrix data center, followed by transfer into the Refseq protein sequence ID. The protein sequence was then obtained using batch entrez from the NCBI Entrez database. The signal peptides were predicted using the SignalP web server (on the world wide web at cbs.dtu.dk/services/SignalP/), based on both Neural networks and Hidden Markov models (Nielsen, H., Engelbrecht, J., Brunak, S. & von Heijne, G. Protein Eng 10, 1-6 (1997), and Bendtsen, J. D., Nielsen, H., von Heijne, G. & Brunak, S. J Mol Biol 340, 783-95 (2004)). Candidate proteins with signal peptides expressed in fetal liver CD3+ cells at a level greater than two-fold that of adult CD3+ and fetal liver Gr-1+ cells were selected for further study.

Production of Coiled-Coil Domain and Fibrinogen-Like Domain of Angptl2

The DNA encoding human Angptl2 fused with FLAG peptide sequence at the c terminus was constructed as Flag-Angptl2. Human Angptl2 and Pro 100-Lys 330 of human IgG1 Fc sequences were linked by a DNA sequence encoding IEGRMD linker peptide (SEQ ID NO.: 1) to form Angptl2-hFc. The whole fragment was inserted into pcDNA3.1, downstream of CMV promoter. The plasmid was transfected into 293T cells using lipofectamine 2000 (Invitrogen) and conditioned medium at 48 hour after transfection was collected. The conditioned medium with about 1 µg/ml of IGF-2-hFc determined by western blotting was used in the subsequent staining of bone marrow cells.

Similar to constructing FLAG-hAngptl2, a cDNA encoding the coiled-coil domain or fibrinogen-like domain of human Angptl2 fragments was generated. The former contained hAngptl2 amino acids Arg 1-Lys 249 and the latter Arg 1-Pro 76 fused to Arg 276-His 493. Both were fused at the C-terminus with a FLAG epitope. FLAG tagged human Fgl1 or human Mfap4 were also constructed with a FLAG fused at the C-terminus of the encoded proteins. These plasmids were transfected into 293T cells and the conditioned medium were collected similar to the procedure for producing FLAG-Angptl2.

Western Blots

Purified proteins or crude proteins in conditioned medium were analyzed by electrophoresis on 4 to 12% NuPage Bis-Tris polyacrylamide gels (Invitrogen), and proteins were electroblotted onto nitrocellulose membranes. The membranes were probed with the horseradish peroxidase-conjugated anti-FLAG M2 monoclonal antibody (Sigma; at 1:5000 dilution) or a combination of human Angptl2-specific primary monoclonal antibodies (in FIG. 1: 1 µg/ml of clone 239829; in FIG. 15A: 1 µg/ml of 239809.11, 239813.111, 239816.111, 239819.111, 239829.111, 239830.11, 239833.11, 239834.11, and 239835.111, all gifts from R&D Systems), incubated with the horseradish peroxidase-conjugated goat-anti-mouse antibody (at 1:2000 dilution) and detected by chemiluminescence with the ECL kit (Amersham, Arlington Heights, Ill.).

Real Time PCR

Total RNA was isolated from indicated fetal liver or bone marrow cell populations. First-strand cDNA was synthesized using SuperScript II RT (Invitrogen). Samples were analyzed in triplicate 25 µl reactions (300 nM of primers, 12.5 µl of Master mix), which was adapted from the standard protocol provided in SyBR Green PCR Master Mix and RT-PCR Protocol provided by Applied Biosystems. Primers were purchased from Qiagen (QT00151179 for Angptl2 and QT00110824 for Angptl3). The default PCR protocol was used on an Applied Biosystems Prism 7000 Sequence Detection System. The mRNA level of Angptl2 and Angptl3 in each population was normalized to the level of 18S RNA transcripts present in the same sample.

Angiopoietin-Like Proteins

FLAG-hAngptl2, the coiled-coil domain of hAngptl2, FLAG-tagged fibrinogen-like domain of hAngptl2, FLAG-hAngptl4, FLAG-hFgl1, and FLAG-hMfap4, were all produced by transient transfection of 293T cells using Lipofectamine 2000 (Invitrogen). After transfection, the cells were cultured overnight in IMDM with 10% FBS, and then washed with IMDM before being cultured in serum-free StemSpan medium (StemCell Technology) for another 24 h. The conditioned medium was harvested and used in experiments in FIGS. 1, 2, and 5b. Medium from mock-transfected cells was always used as a negative control. Serum-free conditioned medium cultured mock-transfected 293T cells for 4 h before addition of purified Angptl2 or Angptl3 was used in the experiments in FIG. 3. To purify FLAG-Angptl2 and FLAG-Angptl4, the corresponding plasmid-transfected 293T cells were cultured in IMDM with 10% FBS for 48 h or 72 h and the conditioned medium was collected for anti-FLAG affinity purification.

Purified mouse angiopoietin-like protein 3 (mAngptl3) was produced in sf21 cells using a baculovirus expression system, and was a gift from R&D Systems. GST-hAngptl5, a fusion protein of GST and human angiopoietin-like protein 5 (hAngptl5) and produced by a cell-free wheat germ in vitro transcription/ translation system, was purchased from Abnova Corporation, Taiwan. Bacterially-expressed hAngptl2 and hAngptl7 were gifts from R&D Systems.

Production of Tagged-Angptl2 and Other FLAG-Tagged Proteins

The cDNA encoding human Angptl2 (Kim, I. et al. J Biol Chem 274, 26523-8 (1999)) fused with a FLAG peptide sequence (as FLAG-hAngptl2) or with Pro 100-Lys 330 of human IgG1 Fc sequence followed by FLAG (as FLAG-hFc-hAngptl2) at the C-terminus was constructed. The DNA was inserted into the pcDNA3.1 (−) vector (Invitrogen) downstream of the CMV promoter. Plasmids were transfected into 293T cells using lipofectamine 2000 (Invitrogen) and the serum-containing conditioned medium was collected at 48 h and 72 h after transfection.

Purification of FLAG-Angptl2 and FLAG-Angptl4

Serum-free conditioned medium as detailed above was harvested after 48-72 h from FLAG-hAngptl2 or FLAG-hAngptl4 transfected 293T cells. One tablet/50 ml of the Complete Protease Inhibitor Cocktail (Roche), 5 µg/ml PMSF, and 100 mM NaCl were added, and the medium was applied to an anti-FLAG epitope immunoaffinity column (Anti-FLAG M2 affinity Gel, Sigma), using 500 µl of resin per 500 ml of conditioned medium. The column was subsequently washed 10 times with a total of 100 volumes of TBS (50 mM Tris, pH 7.4, 150 mM NaCl) and the FLAG-hAngptl2 or FLAG-hAngptl4 was eluted with 0.1 mg/ml FLAG peptide (N-DYKDDDDK-C; SEQ ID NO.: 2) dissolved in TBS.

Cell Culture

Twenty BM SP Sca-1$^+$ CD45$^+$ cells isolated from 6 to 9 or 8 to 10 week old C57BL/6 CD45.2 mice were plated in 100 or 160 µl of StemSpan serum-free medium (StemCell Technologies) supplemented with 10 µg/ml heparin (Sigma), 10 ng/ml mouse SCF, 20 ng/ml mouse TPO, 20 ng/ml mouse IGF-2 (all from R&D Systems), and 10 ng/ml human FGF-1 (Invitrogen), with or without the indicated amounts of angiopoietin-like proteins. In some experiments, the cells were plated in one well of a U-bottom 96-well plate (3799; Corning). As indicated in the individual experiments and detailed above, some of these proteins had been purified, and others were added from the conditioned medium of transfected 293T cells. Medium from mock-transfected cells was always used as a negative control. After 3 to 10 d of culture as indicated, the cells were harvested for competitive transplantation. Unconditioned serum-free medium supplemented with 10 µg/ml heparin, 10 ng/ml mouse SCF, 20 ng/ml mouse TPO, 20 ng/ml mouse IGF-2, and 10 ng/ml human FGF-1 is termed unconditioned STIF medium, and the conditioned medium collected from 293T cells which was then supplemented with the above cytokines is termed conditioned STIF medium. For the purpose of competitive transplantation, cells from at least 6 culture wells were pooled and mixed with competitor cells before the indicated numbers of cells were transplanted into each mouse.

Competitive Reconstitution Analysis

The indicated numbers of CD45.2 donor cells were mixed with 1×10$^5$ or 2×10$^5$ freshly isolated CD45.1 competitor bone marrow cells, and the mixture injected intravenously via the retro-orbital route into each of a group of 6 to 9 week old CD45.1 mice previously irradiated with a total dose of 10 Gy. To measure reconstitution of transplanted mice, peripheral blood was collected at the indicated times post-transplant and the presence of CD45.1$^+$ and CD45.2$^+$ cells in lymphoid and myeloid compartments were measured as described (Zhang, C. C. & Lodish, H. F. Blood 103, 2513-21 (2004) and Zhang, C. C. & Lodish, H. F. Blood 105, 4314-20 (2005)). Briefly, peripheral blood cells were collected by retro-orbital bleeding, followed by lysis of red blood cells and staining with anti-CD45.2-FITC, and anti-CD45.1-PE, or anti-Thy1.2-PE (for T-lymphoid lineage), anti-B220-PE (for B-lymphoid lineage), anti-Mac-1-PE, anti-Gr-1-PE (cells costaining with anti-Mac-1 and anti-Gr-1 were deemed the myeloid lineage), or anti-Ter119-PE (for erythroid lineage) monoclonal antibodies (BD Pharmingen). The "Percent repopulation" shown in all Figures except FIG. 1c and 1d was based on the staining results of anti-CD45.2-FITC and anti-CD45.1-PE. In all cases FACS analysis of the above listed lineages was also performed to confirm multilineage reconstitution. Calculation of CRUs in limiting dilution experiments was conducted using L-Calc software (StemCell Technologies) (Zhang, C. C. & Lodish, H. F. Blood 105, 4314-20 (2005)).

Primary Human Cells

Primary human cord blood cells were purchased from Cambrex (Poietics™ Mononuclear cells from Human Cord Blood, Cat# 2C-150A). Cells were plated at 10$^6$ cells/ml of StemSpan serum-free medium (StemCell Technologies) supplemented with 10 µg/ml heparin (Sigma), 10 ng/ml mouse SCF, 20 ng/ml mouse TPO, 20 ng/ml mouse IGF-2 (all from R&D Systems), and 10 ng/ml human FGF-1 (Invitrogen), and with 100 ng/ml Angptl3 or Angptl5. Medium volume was increased by adding fresh medium at day 5, 8, 12, and 15 to maintain cell densities at 5×10$^5$ to 1.5×10$^6$ cells/ml.

Transplant Into NOD/SCID Mice

Cultured progeny from human mononuclear cord blood cells were collected at the indicated days and injected into sub-lethally irradiated (350 rad) NOD-SCID mice (purchased from Jackson). Two months after transplantation, bone marrow nucleated cells from transplanted animals were analyzed by flow cytometry for the presence of human CD45$^+$ cells. Mice were considered to be positive for human HSC engraftment when at least 0.1% CD45$^+$ human cells were detected among mouse bone marrow cells.

Results

Fetal Liver CD3$^+$ Cells Express Angptl2 and Angptl3

Secreted or membrane proteins that are specifically expressed in E15 mouse fetal liver CD3$^+$ cells but not in two cell populations—adult CD3$^+$ cells and fetal liver Gr-1$^+$ cells—that do not support HSC maintenance or expansion in culture were identified by microarray analysis (Table 1).

TABLE 1

| Name | GI | NP | FLCD3$^+$ (raw) (1) | SpnCD3$^+$ (raw) (2) | FLGr-1$^+$ (raw) (3) | Fold (1)/(2) (Normalized) | Fold (1)/(3) (Normalized) |
|---|---|---|---|---|---|---|---|
| claudin 13 | 10048432 | NP_065250 | 4184.2 | 26.6 | 10.7 | 96.5 | 96.5 |
| RIKEN cDNA 4432416J03 | 21313426 | NP_084345 | 1774.3 | 21.2 | 8.7 | 42.3 | 42.3 |
| chemokine (C—X—C motif) ligand 7 | 12963823 | NP_076274 | 936.2 | 18.7 | 8.0 | 20.7 | 20.7 |
| angiopoietin-like 2 | 31560520 | NP_036053 | 583.2 | 4.2 | 5.8 | 13.8 | 13.8 |
| popeye domain containing 2 | 11612497 | NP_071713 | 581.6 | 4.5 | 3.7 | 9.5 | 9.5 |
| expressed sequence C85492 | 31981988 | NP_705768 | 470.0 | 3.2 | 3.8 | 9.3 | 9.3 |
| RIKEN cDNA 2210020M01 | 34304038 | NP_899082 | 375.1 | 7.5 | 3.3 | 8.0 | 8.0 |
| QIL 1 protein | 23346595 | NP_694792 | 281.5 | 2.2 | 2.2 | 5.8 | 5.8 |
| RIKEN cDNA C730027E14 | 22122497 | NP_666132 | 277.8 | 3.8 | 3.5 | 4.7 | 4.7 |
| RIKEN cDNA 1300010M03 | 28077025 | NP_083209 | 237.7 | 3.1 | 4.1 | 5.3 | 5.3 |
| RIKEN cDNA 4931414P19 | 28077031 | NP_083166 | 214.4 | 2.3 | 2.6 | 3.8 | 3.8 |
| claudin 14 | 34328494 | NP_062373 | 208.5 | 2.9 | 26.4 | 4.8 | 4.8 |
| chemokine (C—C motif) ligand 24 | 9625035 | NP_062523 | 201.1 | 1.9 | 37.1 | 3.2 | 3.2 |
| RIKEN cDNA 1100001I19 | 27370416 | NP_766508 | 182.0 | 2.6 | 2.9 | 4.3 | 4.3 |
| angiopoietin-like 3 | 33469117 | NP_038941 | 171.6 | 2.0 | 15.5 | 3.3 | 3.3 |
| neuritin 1 | 23956286 | NP_705757 | 60.2 | 1.8 | 3.9 | 3.0 | 3.0 |

Figure 11:
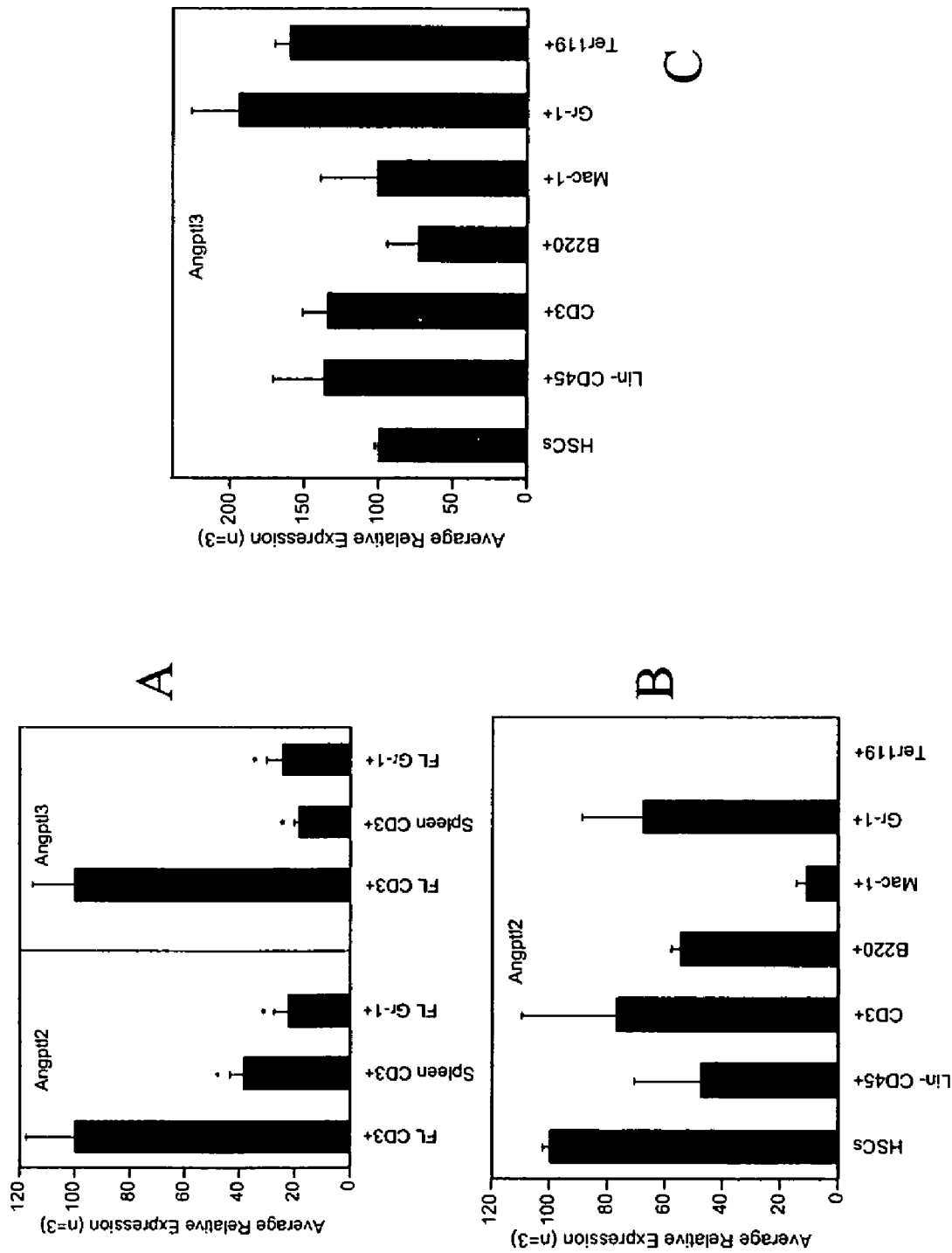
FIG. 11A is a bar graph showing average relative expression of Angptl2 (left panel) or Angptl3 (right panel) mRNA in cells having the indicated phenotype (FL is fetal liver).
FIG. 11B is a bar graph showing average relative expression of Angptl2 mRNA in adult mouse bone marrow hematopoietic cells and adult mouse bone marrow cells having the indicated phenotype.
FIG. 11C is a bar graph showing average relative expression of Angptl3 mRNA in adult mouse bone marrow hematopoietic cells and adult mouse bone marrow having the indicated phenotype.

Both angiopoietin-like 2 (Angptl2) and angiopoietin-like 3 (Angptl3) were found to be secreted proteins specifically expressed in this stem cell supportive population (Table 1, FIG. 11A). These proteins are also found to be expressed in adult bone marrow (BM) cells including the SP CD45$^+$ Sca-1$^+$ highly enriched HSC population (FIG. 11B and FIG. 11C). These two proteins have not previously been implicated in HSC biology.

Freshly Isolated and 4 Day Cultured Bone Marrow HSCs Bind to Angptl 2

Fusion proteins of Angptl2 with the human IgG Fc fragment or FLAG peptide were generated. When these fusion proteins were used to isolate populations of freshly isolated or cultured bone marrow cells that can or cannot bind Angptl2, and followed by reconstitution analysis of them, it was found that Angptl2 is capable of binding to the majority of freshly isolated BM HSCs (FIG. 12A), and to all 4 day cultured HSCs (FIG. 12B). This demonstrates that a receptor for Angptl2 is expressed on most freshly isolated HSCs and all cultured HSCs.

In the experiment shown in FIG. 12A, freshly isolated adult CD45.2 bone marrow cells were incubated at 4° C. for 30 min with conditioned medium from control transfected 293T cells or cells transfected with the Angptl2-hFc—expression vector; the latter medium contained ~1 μg/ml Angptl2-hFc. Cells were then stained with anti-human IgG1-PE. On average 12.8% of total bone marrow cells bind to Angptl2-hFc and 5.3% of 4 day cultured bone marrow cells bind to Angptl2. $5 \times 10^4$ positively stained cells and the same number of negatively stained cells were transplanted together with $2 \times 10^5$ CD45.1 competitor cells into lethally irradiated CD45.1 mice (n=4-5). Peripheral blood cells were analyzed for the presence of CD45.2$^+$ cells in lymphoid and myeloid compartments at 3 weeks and 4 months after transplant.

In the experiment shown in FIG. 12B, adult CD45.2 bone marrow cells were cultured in serum-free medium with SCF, TPO, IGF-2, and FGF-1 as described (Reya, T. et al. Nature 423, 409-14 (2003)) for 4 days. The cells were then stained with Flag-Angptl2—containing medium (~1 μg/ml Flag-Angptl2) as the same as described in FIG. 3. 5.3% of total cells bind to Angiopoietin-FLAG. 1300 positively stained cells and 8000 negatively stained cells were transplanted together with $2 \times 10^5$ CD45.1 competitor cells into lethally irradiated CD45.1 mice (n=4). Peripheral blood cells were analyzed for the presence of CD45.2$^+$ cells in lymphoid and myeloid compartments at 3 weeks and 3 months after transplant.

Angptl2 and Angptl3 Stimulate Ex Vivo Expansion of HSCs

Figure 1:
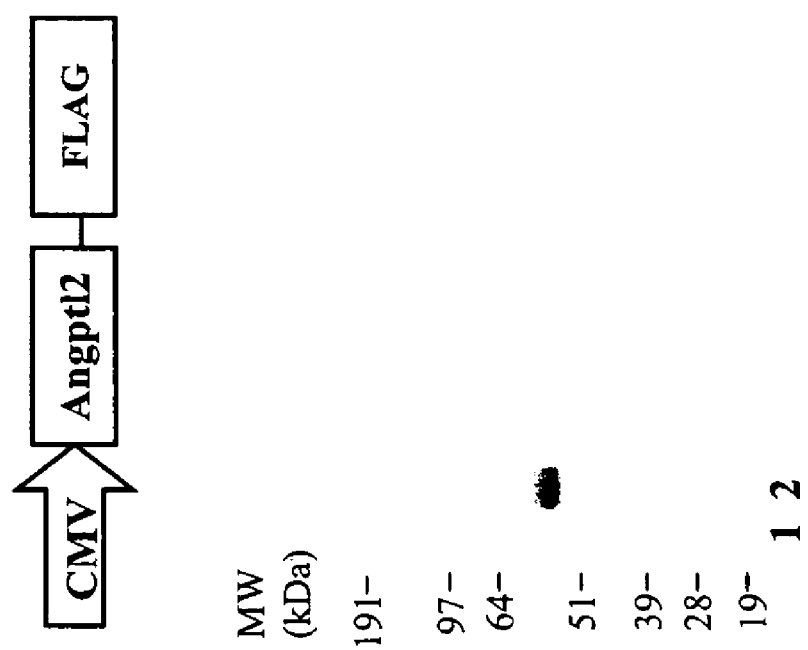
FIG. 1 upper panel shows a schematic of the plasmid expressing the human Angptl2 protein fused to a FLAG epitope at the C-terminus, and the bottom panel shows a Western blot of the 48 h conditioned medium of 293T cells transfected by pcDNA3.1(−) (lane 1) or pcDNA3.1(−) encoding FLAG-Angptl2 (lane 2), probed with antibodies against FLAG epitope.
Figure 12:
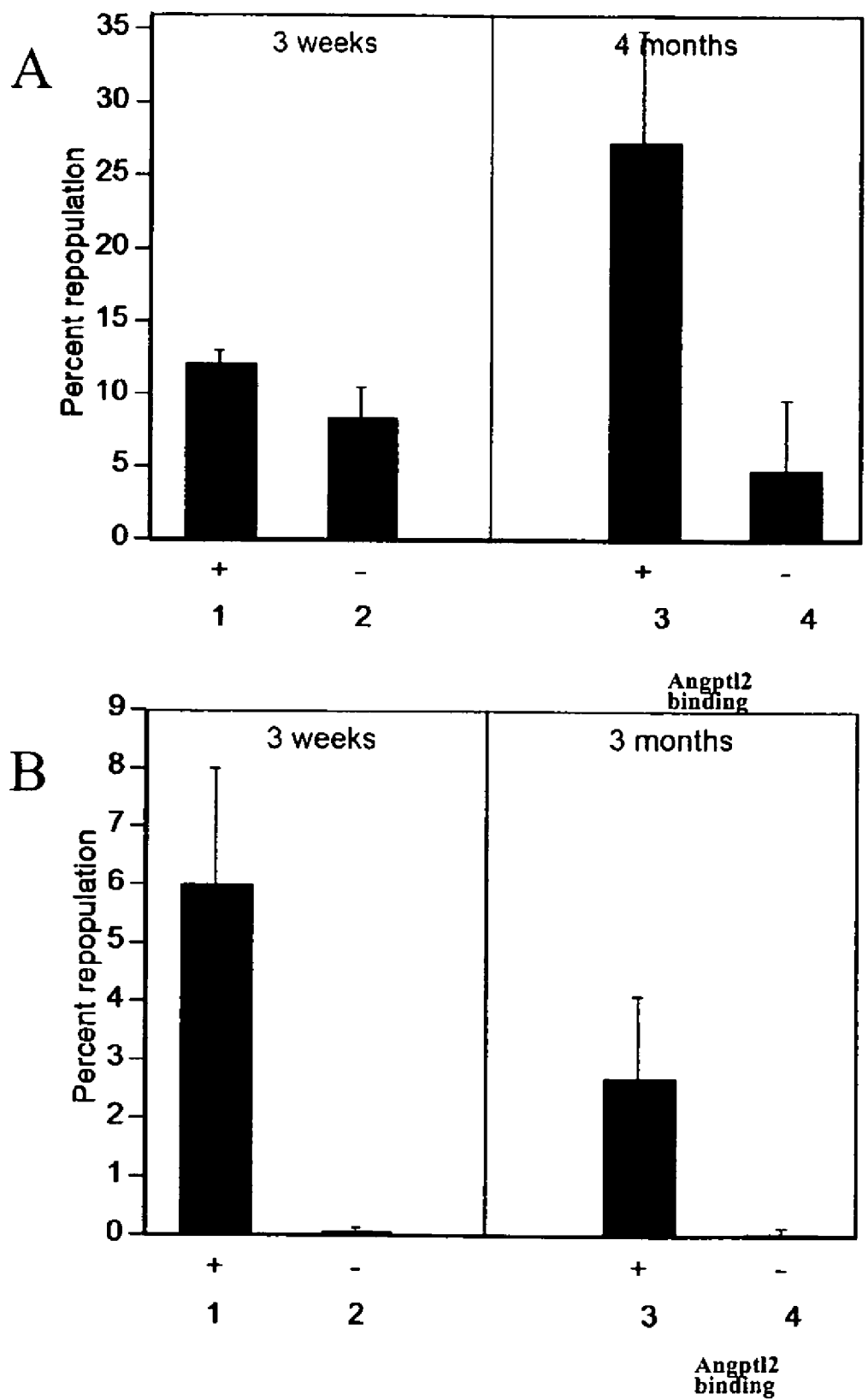
FIG. 12A is a bar graph showing percent repopulation 3 weeks or 4 months after transplant with freshly isolated adult CD45.2 BM cells that either bind Angptl2 or not, as indicated; demonstrating that freshly isolated HSCs bind Angptl2.
FIG. 12B is a bar graph showing percent repopulation 3 weeks or 3 months after transplant with adult CD45.2 BM cells cultured in serum-free medium with SCF, TPO, IGF-2, and FGF-1 for 4 d and that bind Angptl2 or not, as indicated; demonstrating that 4-day cultured HSCs bind Angptl2.

A plasmid containing the entire coding sequence for human Angptl2 with a FLAG tag fused at the C-terminus in the eukaryotic expression vector pcDNA3.1(–) (FLAG-Angptl2) was constructed. Following transient transfection of 293T cells, the culture supernatant contained secreted FLAG-Angptl2 migrating with the expected ~60 kD size (FIG. 1). As shown herein, the majority of freshly isolated LT-HSCs and all LT-HSCs cultured for 4 d bound this hormone (FIG. 12).

Figure 2:
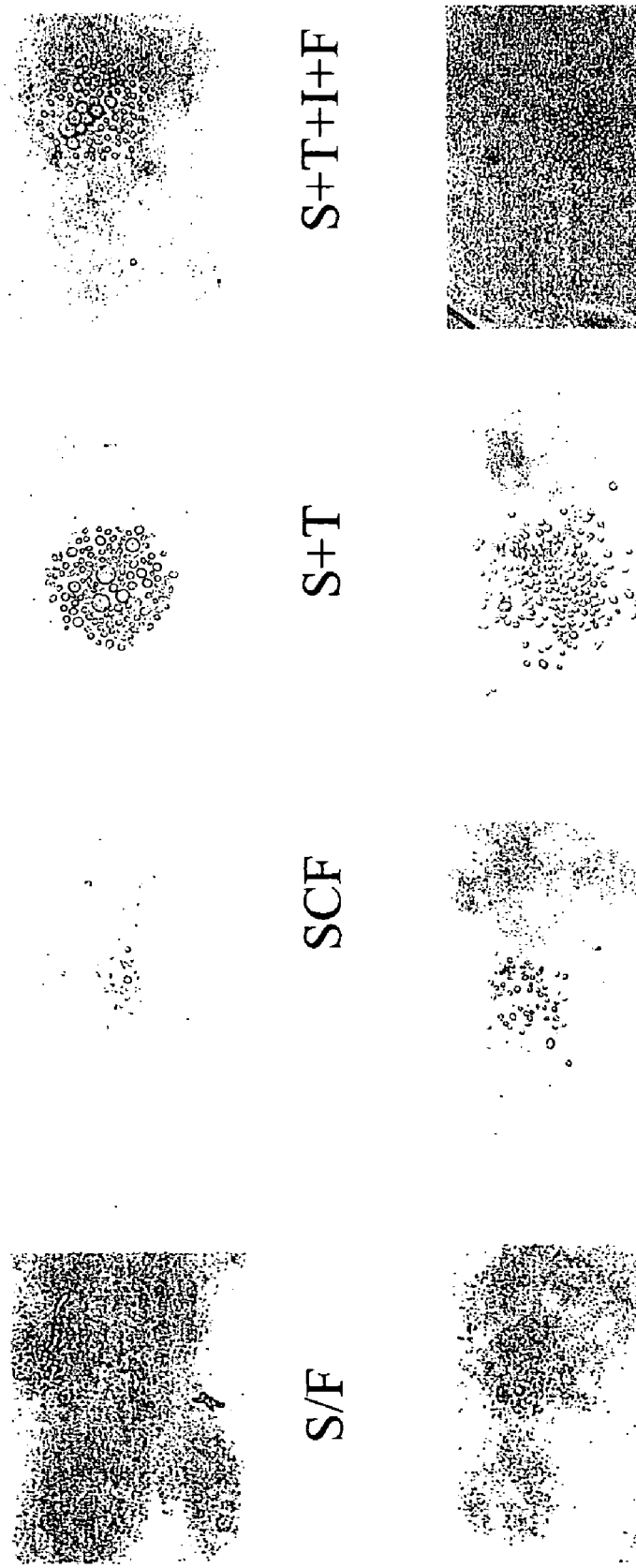
FIG. 2 shows micrographs of FACS sorted bone marrow SP Sca-1+ CD45+ cells in various serum-free culture conditions, with and without Angptl2.

In the experiment shown in FIG. 2, twenty CD45.2 bone marrow SP Sca-1$^+$ CD45$^+$ cells were seeded into each well of a 96-well U-bottom plate, in serum-free conditioned medium collected from mock transfected 293T cells (S/F: serum-free medium, SCF: serum-free medium with 10 ng/ml SCF, S+T: serum-free medium with 10 ng/ml SCF and 20 ng/ml TPO, S+T+I+F: serum-free medium with 10 ng/ml SCF, 20 ng/ml TPO, 20 ng/ml IGF-2, and 10 ng/ml FGF-1), or in serum-free conditioned medium from 293T cells transfected with Flag-Angptl2 (S/F+Angptl2: serum-free medium with ~100 ng/ml Angptl2, S+A: serum-free medium with 10 ng/ml SCF and ~100 ng/ml Angptl2, S+T+A: serum-free medium with 10 ng/ml SCF, 20 ng/ml TPO, and ~100 ng/ml Angptl2, S+T+I+F+A: serum-free medium with 10 ng/ml SCF, 20 ng/ml TPO, 20 ng/ml IGF-2, 10 ng/ml FGF-1, and ~100 ng/ml Angptl2). Images shown were taken after 3 days of culture, under a phase-contrast microscope.

Figure 3A:
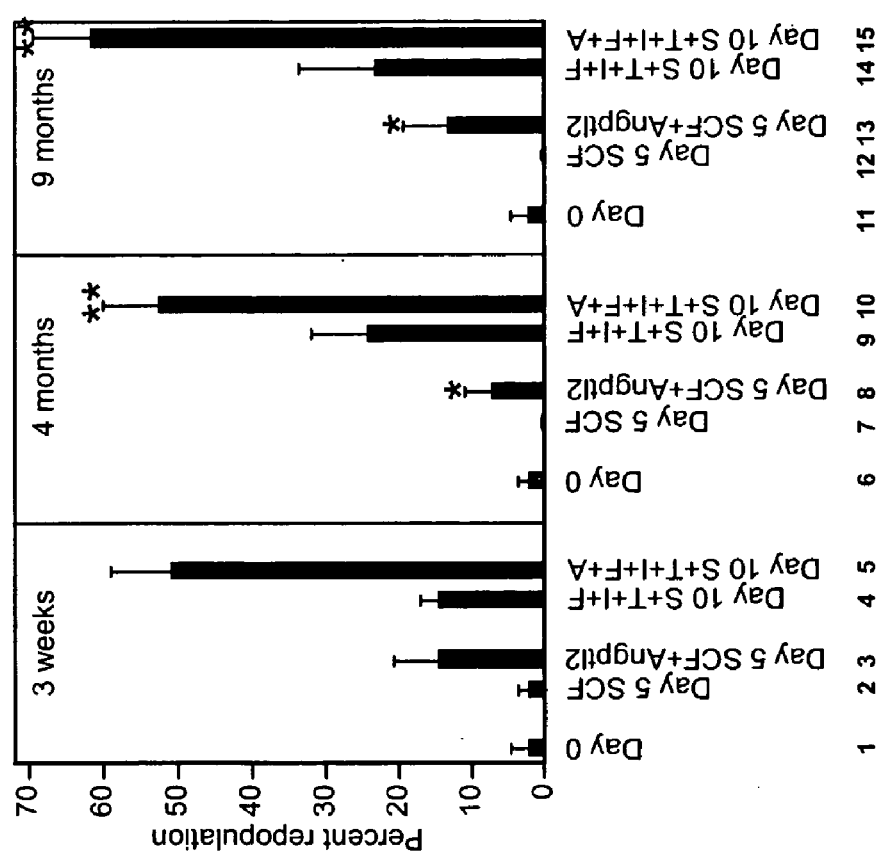
FIG. 3A is a bar graph showing bar percent repopulation 3 weeks, 4 months, and 9 months after transplant with twenty freshly isolated CD45.2 bone marrow SP Sca-1+ CD45+ cells cotransplanted with 1×10$^5$ CD45.1 competitors in the absence of prior culturing (bars 1, 6, and 11) or cultured as indicated.
Figure 3B:
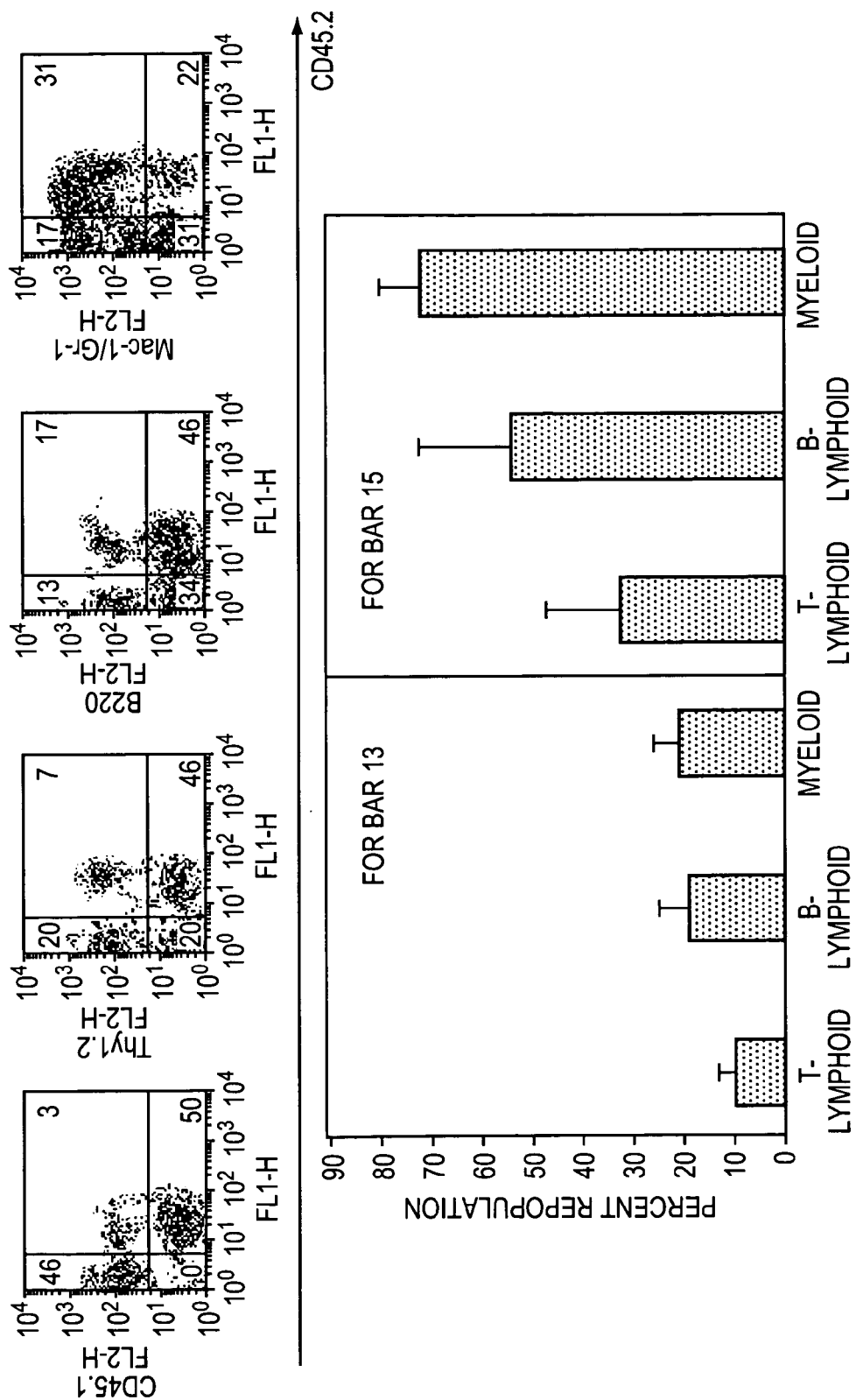
Figure 3C:
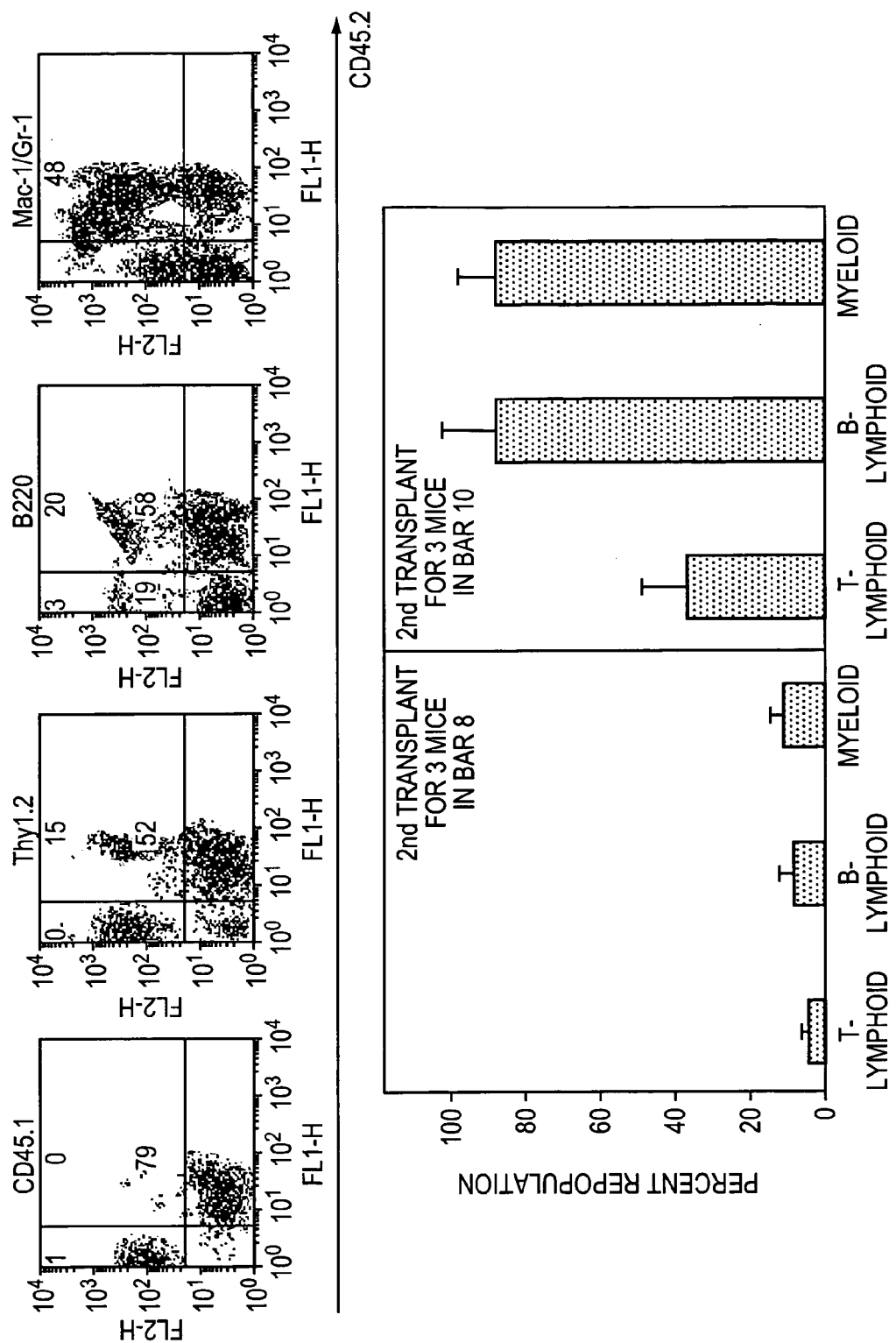

A representative of two independent experiments (FIG. 3A) shows that Angptl2 is a stimulator of ex vivo expansion of LT-HSCs. In this study Angptl2 was not purified but was contained in the conditioned medium of 293T cells transfected with a FLAG-Angptl2 expression vector; conditioned medium from mock-transfected cells served as a negative control. When 20 adult BM SP CD45$^+$ Sca-1$^+$ cells, a highly enriched HSC population (Camargo, F. D., Green, R., Capetanaki, Y., Jackson, K. A. & Goodell, M. A. Nat Med 9, 1520-7 (2003)), were cultured for 5 d in serum-free medium supplemented with SCF, essentially all long-term (LT)-HSC activity was lost, measured by competitive reconstitution (FIG. 3A, compare bars 7 and 12 to bars 6 and 11, respectively). After culture in the same medium with SCF and 100 ng/ml FLAG-Angptl2 for 5 d, LT-HSC activity was dramatically increased (compare bars 8 and 13 to bars 7 and 12, respectively). Similarly, HSCs cultured for 10 d in the presence of SCF, TPO, IGF-2, FGF-1 and Angptl2 achieved a tremendous increase of LT-HSC activity compared to culture in the same medium without Angptl2 (compare bars 10 and 15 to bars 9 and 14, respectively). Stem cells cultured in the presence of Angptl2 repopulated both lymphoid and myeloid lineages of the primary recipients at 9 months post-transplant (FIG. 3B) as well as in secondary transplanted mice (FIG. 3C), indicating a net expansion of LT-HSCs. After 9 months following transplants all mice were healthy and no tumors were observed. Addition of 100 ng/ml FLAG-Angptl2 also caused an increase in expansion of ST-HSC activity, measured at 3 weeks post-transplant (compare bar 3 with 2, and 5 with 4).

Importantly, culturing highly enriched HSCs in serum-free medium containing SCF, TPO, IGF-2, and FGF-1 was found to result in an 8-fold increase of LT-HSC numbers (Zhang, C. C. & Lodish, H. F. Blood 105, 4314-20 (2005)). An additional increase in the extent of HSC expansion by adding Angptl2 was observed. Therefore, Angptl2 is a novel growth factor for HSCs, whose effect is synergistic with other HSC growth factors.

Figure 4:
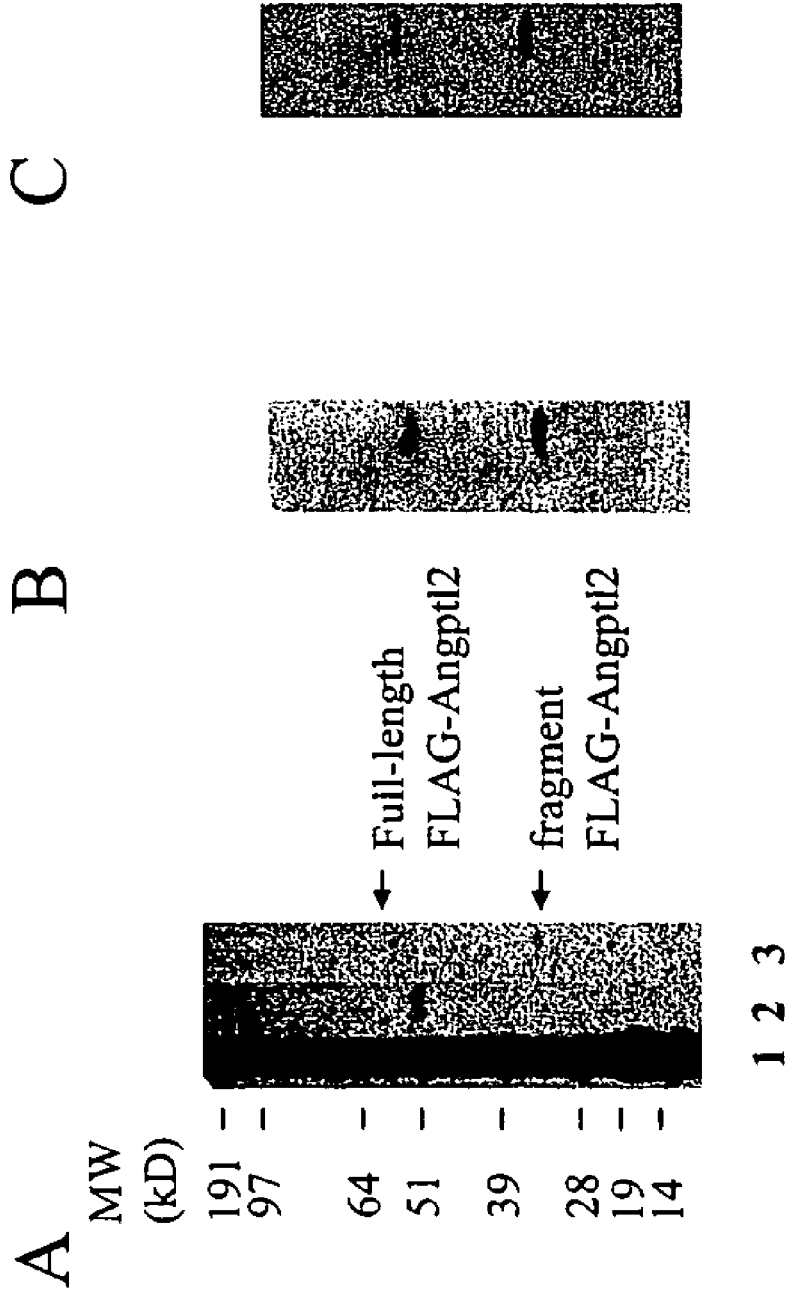
FIG. 4A shows a silver stain of 16 ng of purified E. coli-expressed Angptl2 (lane 2), and 2.5 ng of purified mammalian-expressed FLAG-Angptl2 protein (purified from an anti-FLAG column, lane 3) fractioned by SDS-PAGE.
FIG. 4B shows a Western blot of the purified Angptl2 (right lane) and control (left lane) probed with anti-FLAG antibody.
FIG. 4C shows a Western blot of the purified Angptl2 (right lane) and control BSA (left lane) probed with anti-Angptl2 mAb.

To isolate pure recombinant Angptl2, conditioned medium from FLAG-Angptl2 transfected 293T cells was collected and the FLAG-tagged protein was purified by immunoaffinity chromatography using an immobilized monoclonal antibody specific for the FLAG epitope. SDS-PAGE of the eluted fraction showed two major bands, one at the position expected for the full-length FLAG-Angptl2 (~60 kDa), and the other a smaller peptide of ~36 kDa (FIG. 4A, lane 3). The mammalian-expressed full-length FLAG-Angptl2 had a higher molecular weight than bacterially-expressed Angptl2 (compare lane 3 to lane 2), consistent with a previous result that mammalian-expressed Angptl2 is glycosylated (Kim, I. et al. J Biol Chem 274, 26523-8 (1999)). Western blotting with an anti-FLAG M2 antibody, which recognizes the C-terminal FLAG epitope, stained both bands (FIG. 4B) as did an Angptl2-specific monoclonal antibody (FIG. 4C). Thus the FLAG-Angptl2 underwent partial proteolysis during purification.

Figure 5:
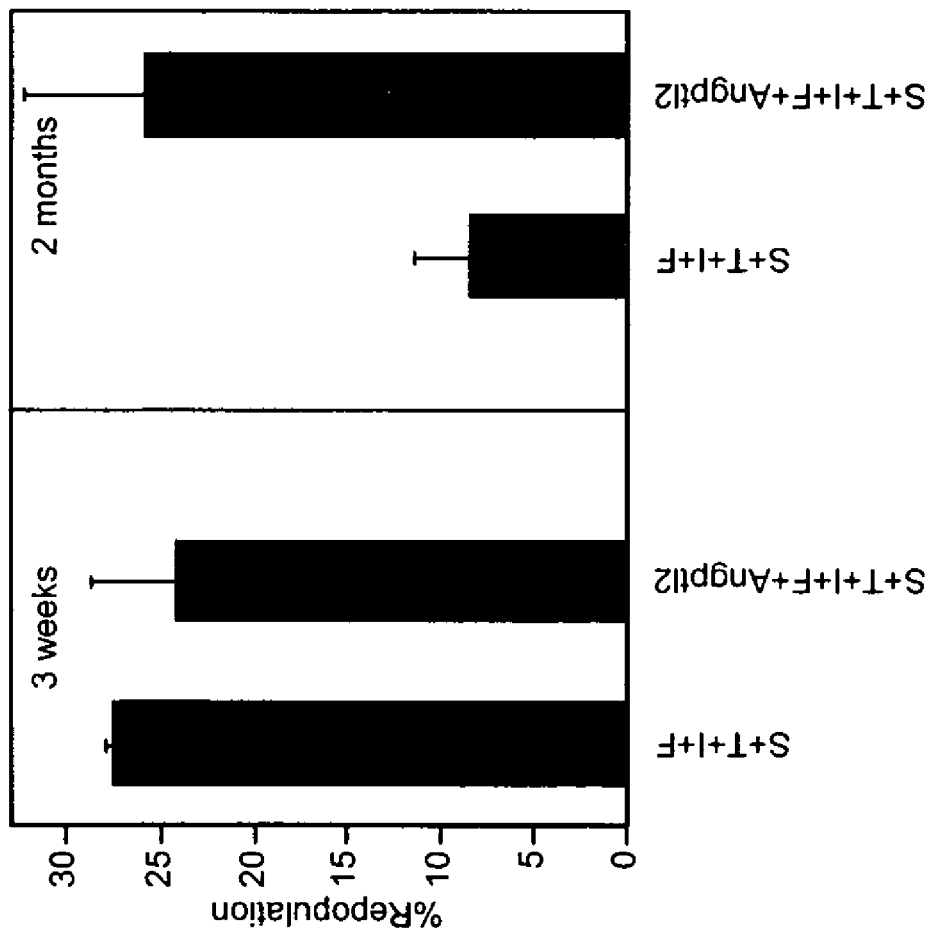
FIG. 5 is a bar graph showing that purified Angptl2 is a growth factor for HSCs.

As shown in FIG. 5, purified mammalian-expressed Angptl2 stimulated the proliferation of hematopoietic stem cells. Twenty CD45.2 bone marrow SP Sca-1$^+$ CD45$^+$ cells were cultured for 10 days in serum-free medium with 10 ng/ml SCF, 20 ng/ml TPO, 20 ng/ml IGF-2, and 10 ng/ml FGF-1, or in the same medium with 100 ng/ml purified Flag- Angptl2 (as in FIG. 4). Then the cells were cotransplanted with 1×10⁵ CD45.1 competitors into CD45.1 recipients (n=5). Engraftment 3 weeks (left panel) and 2 months (right panel) post-transplant were shown.

Figure 7:
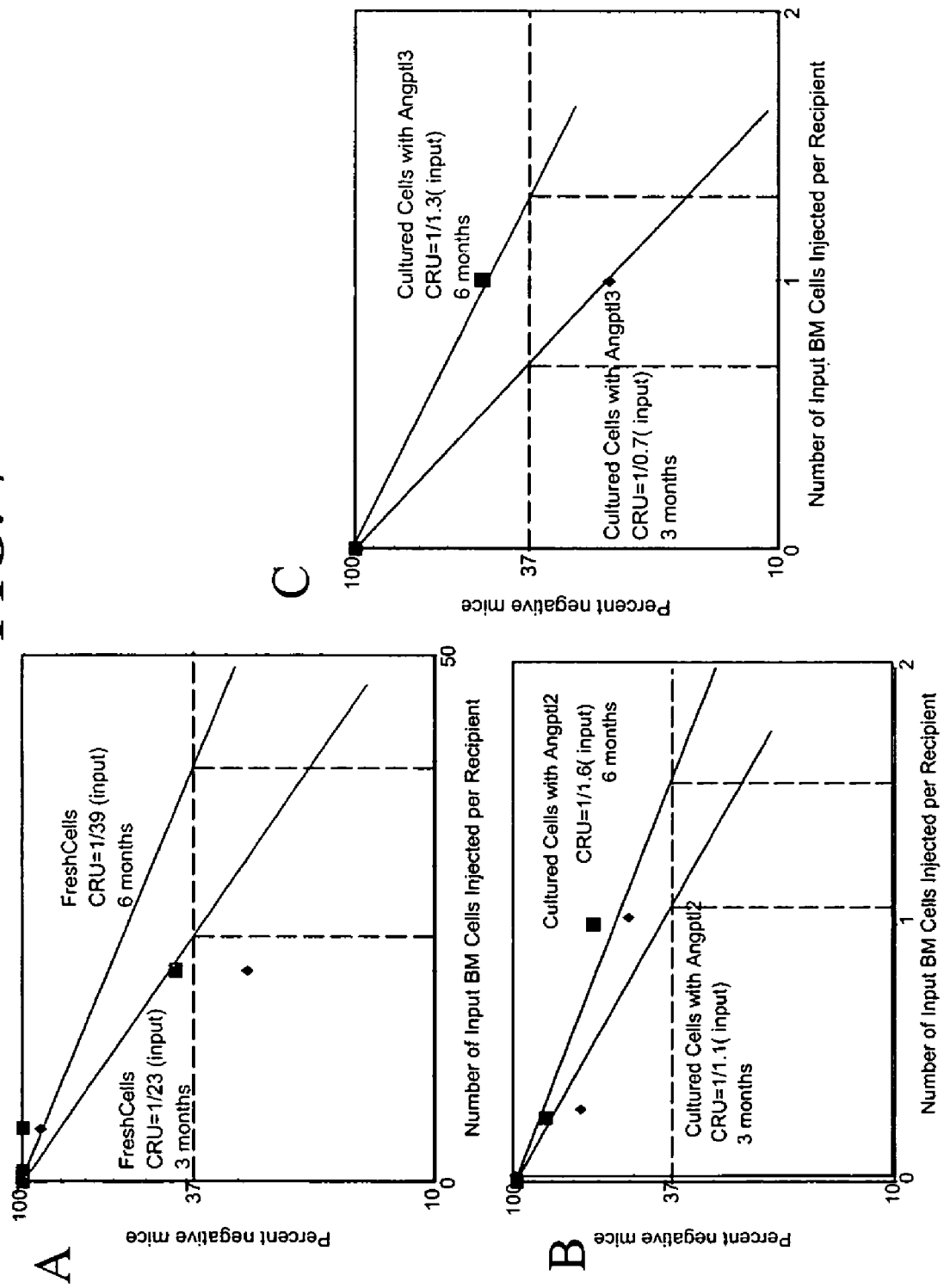
FIG. 7A is a graph showing percent of mice repopulated with the indicated number of BM SP CD45$^+$Sca-1$^+$ cells.
FIG. 7B is a graph showing percent of mice repopulated with the indicated number of BM SP CD45$^+$Sca-1$^+$ cells after culturing for 10 d in serum-free conditioned STIF medium containing 100 ng/ml of purified Angptl2.
FIG. 7C is a graph showing percent of mice repopulated with the indicated number of BM SP CD45$^+$Sca-1$^+$ cells after culturing for 10 d in serum-free conditioned STIF medium containing 100 ng/ml of purified Angptl3.

The limiting dilution competitive repopulation assay in FIG. 7 shows that culture of purified HSCs with Angptl2 or Angptl3, together with other growth factors, results in a greater than 20-fold expansion of LT-HSC numbers. The frequency of long-term repopulating cells (CRU) in freshly isolated BM SP CD45$^+$ Sca-1$^+$ cells is 1 per 23 at 3 months post-transplant (95% confidence interval for mean: 1/15 to 1/35, n=25; FIG. 7A, bottom line) or 1 in 39 at 6 months post-transplant (95% confidence interval for mean: 1/24 to 1/63; FIG. 7A, top line). That is, as calculated from Poisson statistics, injection of on average of 23 or 39 freshly isolated BM SP CD45$^+$ Sca-1$^+$ cells is sufficient to repopulate 63% (=1−1/e) of transplanted mice. After the cells were cultured for 10 d in serum-free conditioned STIF medium with Angptl2, the number of cells was too few to be counted reliably. However, based on the number of cells initially added to the culture, the CRU of the cultured cells was 1/1.1 at 3 months post-transplant (FIG. 7B, bottom line; 95% confidence interval for mean: 1/0.5 to 1/2.3, n=30) or 1/1.6 at 6 months post-transplant (FIG. 7B, top line; 95% confidence interval for mean: 1/1.1 to 1/2.3). In other words, injection of the cultured progeny of only 1.1 or 1.6 freshly isolated BM SP CD45$^+$ Sca-1$^+$ cells is sufficient to repopulate 63% of the mice. Thus the data in FIG. 7B shows that the number of LT-HSCs (6 months post-transplant) increases 24 fold (=39/1.6) after culture.

The same strategy was used to measure the effect of purified Angptl3. The CRU of the cultured cells was 1/0.7 at 3 months post-transplant (FIG. 7C, bottom line; 95% confidence interval for mean: 1/0.3 to 1/1.7, n=24) or 1/1.3 at 6 months post-transplant (FIG. 7C; top line; 95% confidence interval for mean: 1/0.9 to 1/2.0), again relative to the number of cells initially added to the culture. Therefore, culture of BM SP CD45$^+$ Sca-1$^+$ cells in the presence of purified Angptl3 for 10 d results in a 30 (=39/1.3) fold expansion of repopulating LT-HSCs (6 months post-transplant).

Figure 6:
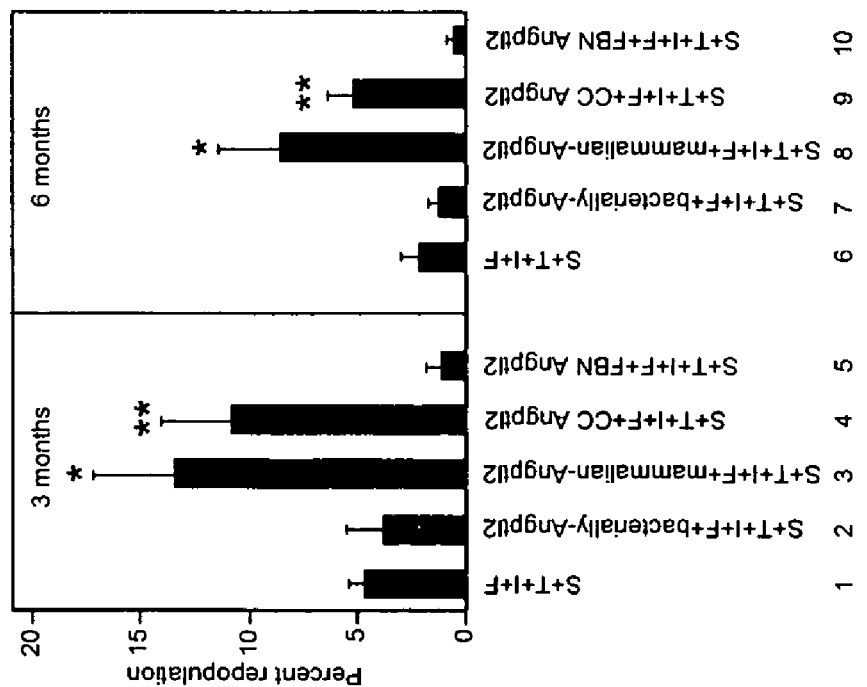
FIG. 6 left panel shows a Western blot of 48 hour conditioned medium of 293T cells transfected by pcDNA3.1(−) (lane 1), FLAG-hAngptl2 coiled-coil domain (lane 2), or FLAG-hAngptl2 fibrinogen-like domain (lane 3), probed with antibodies against hAngptl2; the right panel is a bar graph showing percent repopulation 3 months and 6 months after transplant with twenty CD45.2 bone marrow SP Sca-1$^+$ CD45$^+$ cells cultured for 5 d in serum-free mock-transfected 293T cell conditioned STIF medium (bars 1 and 6); in the same medium with 100 ng/ml E. coli-expressed full-length Angptl2 (bars 2 and 7); and in the same medium with 100 ng/ml mammalian-expressed full-length Angptl2 (bars 3 and 8).
Figure 6:
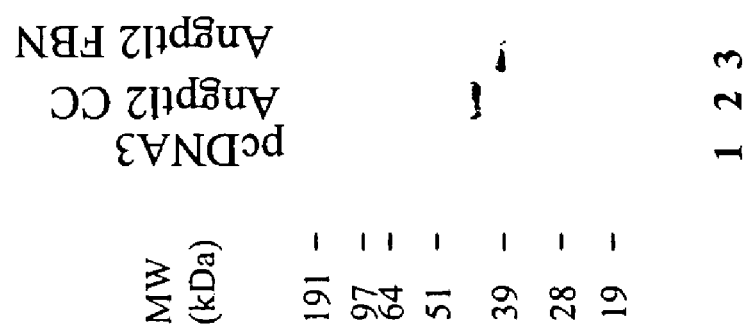

Expansion of HSC activity by Angptl3, like that by Angptl2, was highly reproducible. In two additional experiments, progenies of 20 BM SP CD45$^+$ Sca-1$^+$ cells after 10 d of culture in serum-free conditioned STIF medium with 100 ng/ml Angptl3 showed 65.3%±4.0% and 73.1%±3.1% (n=5) of engraftments respectively at 4 months post-transplant. Thus the culture system consistently achieved dramatic increases of the repopulation activities of HSCs. FIG. 6 shows that mammalian cell-specific posttranslational modifications of Angptl2 facilitate its stimulation of ex vivo HSC expansion. Confirming the result in FIG. 3A, addition of 100 ng/ml mammalian-expressed Angptl2 significantly increased HSC activity after culture (FIG. 6, compare bars 3 and 8 to bars 1 and 6, respectively). By contrast, 100 ng/ml bacterially-expressed Angptl2 was unable to stimulate HSC expansion over STIF medium alone (FIG. 6, compare bars 2 and 7 to bars 1 and 6, respectively). This suggests that some mammalian-specific modification, presumably glycosylation (see FIG. 4A, lanes 2 and 3), positively correlates with the ability of Angptl2 to stimulate LT-HSC expansion. The coiled-coil domain of Angptl2 also stimulated ex vivo HSC expansion (right panel of FIG. 6, compare bars 4 and 9 to bars 1 and 6, respectively).

Several Angptl Family Members Stimulate HSC Expansion.

Angptl2 and Angptl3 belong to a family of angiopoietin-like proteins (Oike, Y., Yasunaga, K. & Suda, T. Int J Hematol 80, 21-8 (2004)). FIG. 5 shows that several members of this family, like Angptl2 and Angptl3, are capable of stimulating HSC expansion in culture. The effects of purified Angptl3, Angptl5, or Angptl7, as well as the coiled-coil domain of Angptl2, Angptl4, or Microfibrillar-associated glycoprotein 4 (Mfap4) in 293T conditioned medium were tested for stimulation of ex vivo expansion of HSCs. All these factors support the increase of HSC activity after culture.

Figure 8:
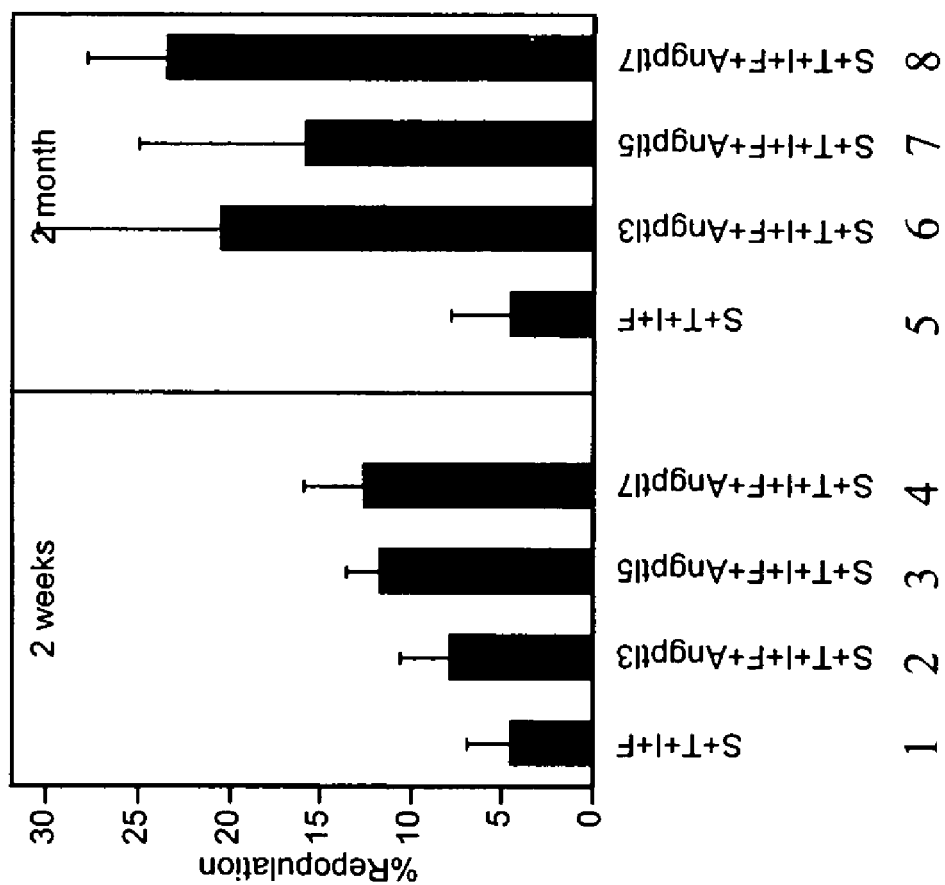
FIG. 8 is a bar graph showing that purified Angptl3, Angptl5, and Angptl7 are growth factors for hematopoietic stem cells.

As shown in FIG. 8, Angptl2-coiled coil domain, Angptl4, and Mfap4 expressed in 293T cell conditioned medium stimulated the proliferation of hematopoietic stem cells. Twenty CD45.2 bone marrow SP Sca-1$^+$ CD45$^+$ cells were cultured for 5 days in serum-free mock transfected conditioned medium with 10 ng/ml SCF, 20 ng/ml TPO, 20 ng/ml IGF-2, 10 ng/ml FGF-1 (lanes 1 and 8), in conditioned medium with the same factors and full-length Angptl2 (lanes 2 and 9), Angptl2 coiled-coil domain (lanes 3 and 10), Angptl2 fibrinogen-like domain (lanes 4 and 11), Angptl4 (lanes 5 and 12), Fibrinogen-like 1 (lanes 6 and 13), or Microfibril-associated glycoprotein 4 (lanes 7 and 14). The cells were then cotransplanted with 1×10⁵ CD45.1 competitors into CD45.1 recipients (n=5). Engraftment 2 weeks (left panel) and 1 month (right panel) post-transplant are shown.

FLAG-tagged Angptl4 was generated by transient transfection of 293T cells followed by immunoaffinity purification using an immobilized anti-FLAG monoclonal antibody. In addition, purified Angptl3 (produced in sf21 cells using a baculovirus system), GST-fused Angptl5 (produced by a cell-free wheat germ in vitro transcription/translational system), and Angptl7 (produced by a bacterial expression system) (left panel, FIG. 10A) were obtained.

Figure 9:
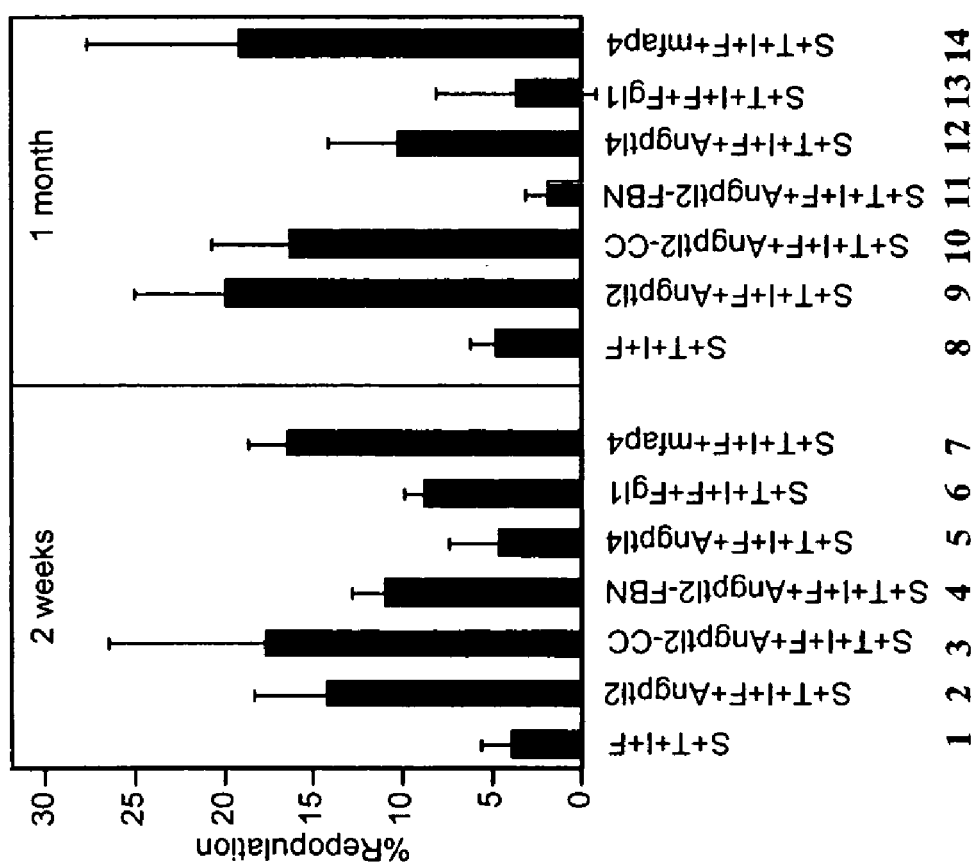
FIG. 9 is a bar graph showing that Angptl2-coiled coil domain, Angptl4, and Mfap4 expressed in 293T cell conditioned medium stimulated the proliferation of hematopoietic stem cells.
Figure 10A:
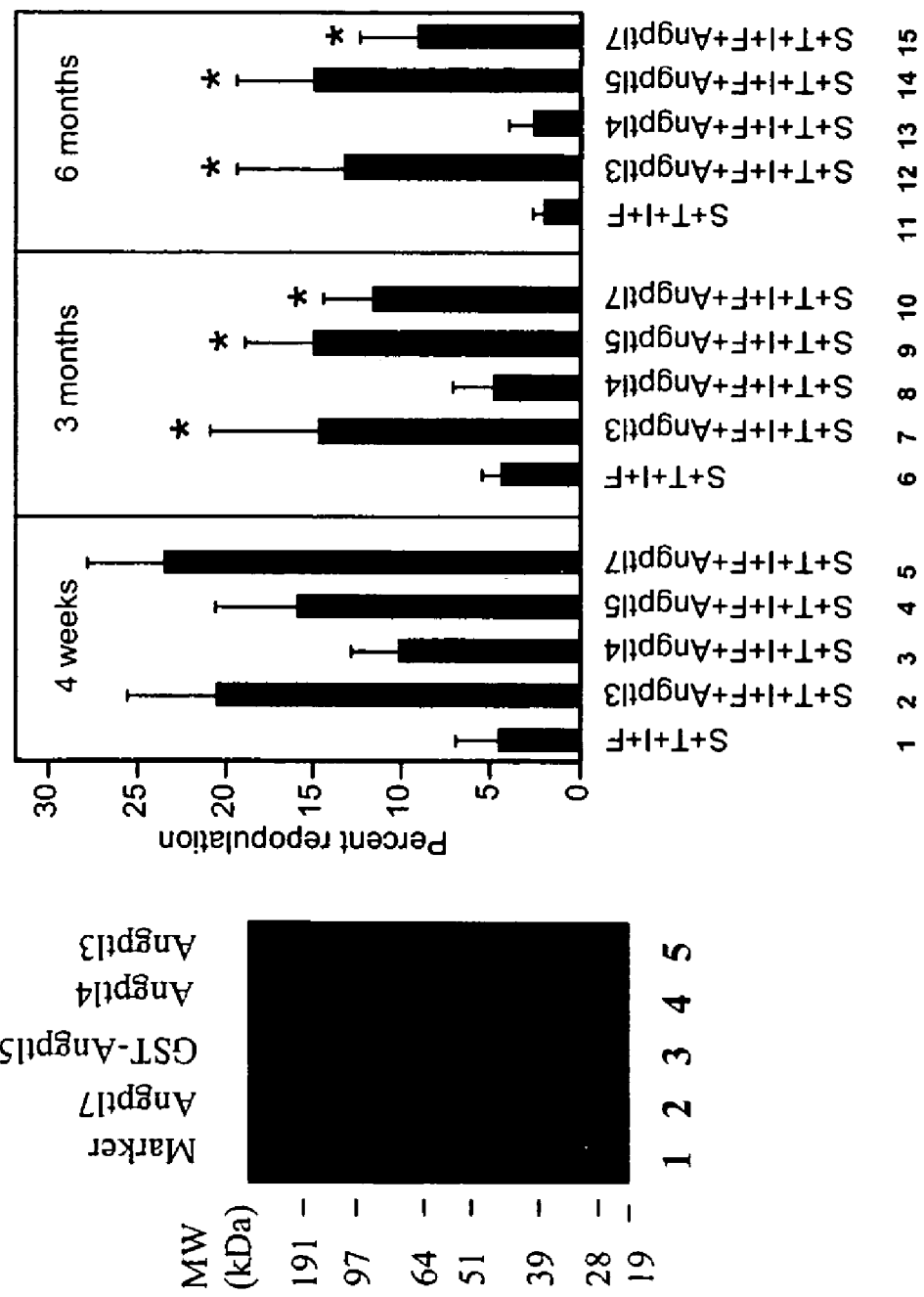
FIG. 10A left panel shows a silver stain of purified bacterially-expressed hAngptl7 (lane 2), purified wheat germ in vitro transcribed GST-hAngptl5 (lane 3), purified mammalian-expressed hAngptl4 (lane 4), and purified sf21-expressed mAngptl3 (lane 5) fractioned by SDS-PAGE; the right panel shows a bar graph of percent repopulation 4 weeks, 3 months, or 6 months after transplant with twenty CD45.2 bone marrow SP Sca-1$^+$ CD45$^+$ cells cultured for 5 d in serum-free unconditioned STIF medium (bars 1, 6, and 11), or cultured in the same medium with 100 ng/ml purified insect-expressed mAngptl3 (bars 2, 7, and 12), or cultured in the same medium with 100 ng/ml purified hAngptl4 (bars 3, 8, and 13), or cultured in the same medium with 100 ng/ml purified GST-hAngptl5 (bars 4, 9, and 14), or cultured in the same medium with 1 μg/ml purified bacterially-expressed hAngptl7 (bars 5, 10, and 15).

Bone marrow SP Sca-1$^+$ CD45$^+$ cells were cultured for 5 d in serum-free unconditioned STIF medium, in the presence of 100 ng/ml of Angptl3, Angptl4, Angptl5, or 1 µg/ml of Angptl7 (FIG. 10A). Addition of Angptl3 to the culture stimulated both ST-HSC and LT-HSC expansion (FIG. 10A, compare bars 2, 7, and 12 to bars 1, 6, and 11, respectively). A significant increase of both ST- and LT-HSC activities was also observed after culture with Angptl5, and also 1 µg/ml of bacterially-expressed Angptl7 (compare bars 1, 6, and 11 to bars 4, 9, and 14, as well as bars 5, 10, and 15, respectively). Angptl4 stimulated at least some HSC activity when tested at 2 weeks and 1 month post transplant (FIG. 9). However, 100 ng/ml Angptl4 was ineffective in stimulating HSC expansion at 3 months and 6 months (FIG. 10, compare bars 3, 8, and 13).

Figure 10B:
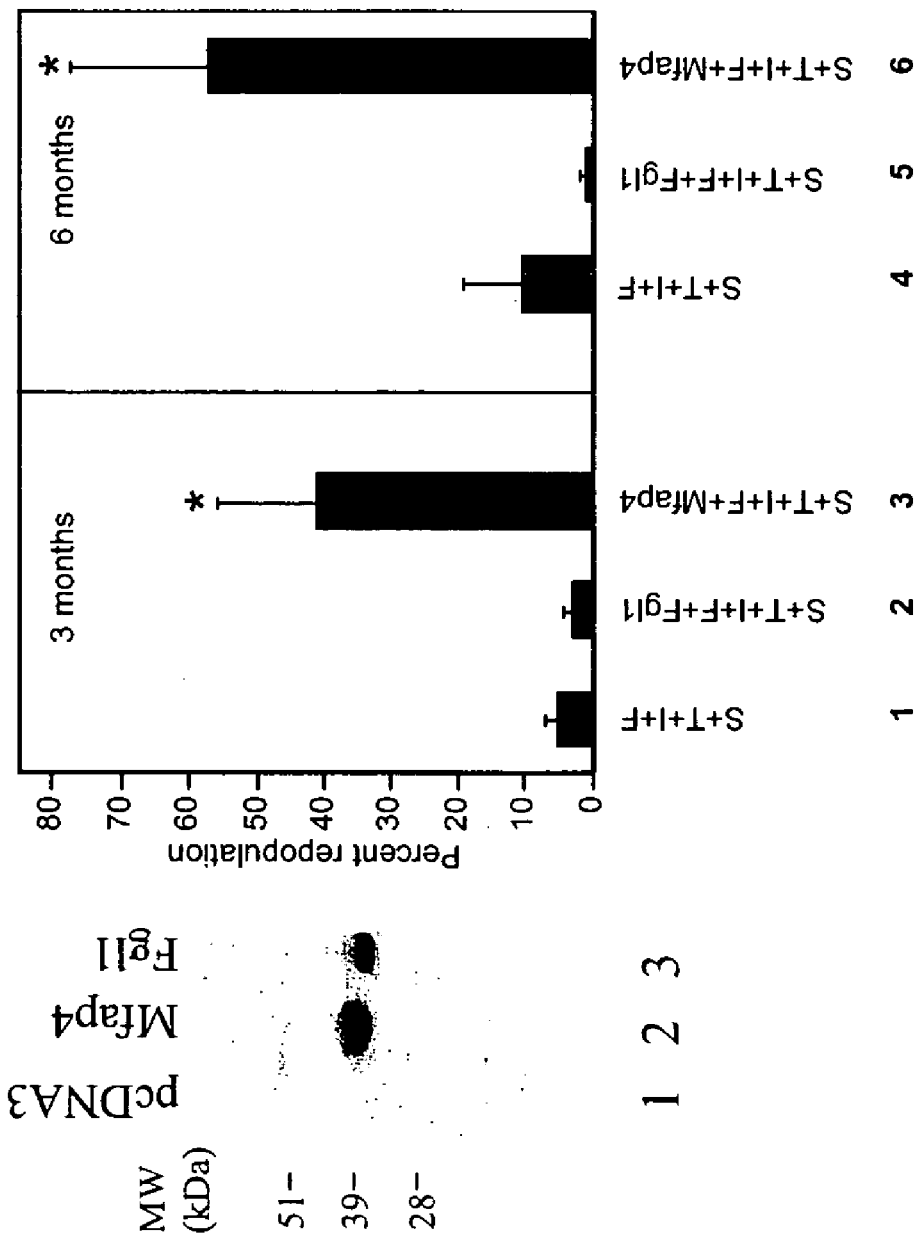
FIG. 10B left panel shows a Western blot of 48 hour conditioned medium of 293T cells transfected by pcDNA3.1(−) (lane 1), pcDNA3.1 encoding FLAG-hMfap4 (lane 2), or pcDNA3.1 encoding FLAG-hFgl1 (lane 3), and probed with an antibody specific for the FLAG epitope; the right panel shows a bar graph of percent repopulation 3 months or 6 months after transplant with twenty CD45.2 bone marrow SP Sca-1$^+$ CD45$^+$ cells cultured for 5 d in serum-free mock transfected conditioned STIF medium (bars 1 and 4), in conditioned STIF medium from 293T cells transfected by pcDNA3.1 encoding FLAG-hFgl1 (bars 2 and 5), or conditioned STIF medium from 293T cells transfected by PCDNA3.1 encoding FLAG-hMfap4 (bars 3 and 6).

The effects of two orthologs of Angptls, microfibrillar-associated glycoprotein 4 (Mfap4) (Zhao, Z. et al. Hum Mol Genet 4, 589-97 (1995)) and fibrinogen-like 1 (Fgl1) (Yamamoto, T. et al. Biochem Biophys Res Commun 193, 681-7 (1993)) were also tested. Both full-length proteins were FLAG-tagged and generated by transient transfection of 293T cells. They were secreted into the medium and detected by Western blotting (FIG. 10B, left panel). Both ~100 ng/ml FLAG-Mfap4 and FLAG-Fgl1 were applied to HSCs directly in the serum-free conditioned STIF medium (FIG. 10B). Competitive reconstitution analysis demonstrated that Mfap4 did stimulate ex vivo expansion of BM SP Sca-1$^+$ CD45$^+$ LT-HSCs after a 5 d culture whilst Fgl1 did not (FIG. 10B).

Angptl 5 Stimulates HSC Activity in Human Cord Blood Cells

Figure 13:
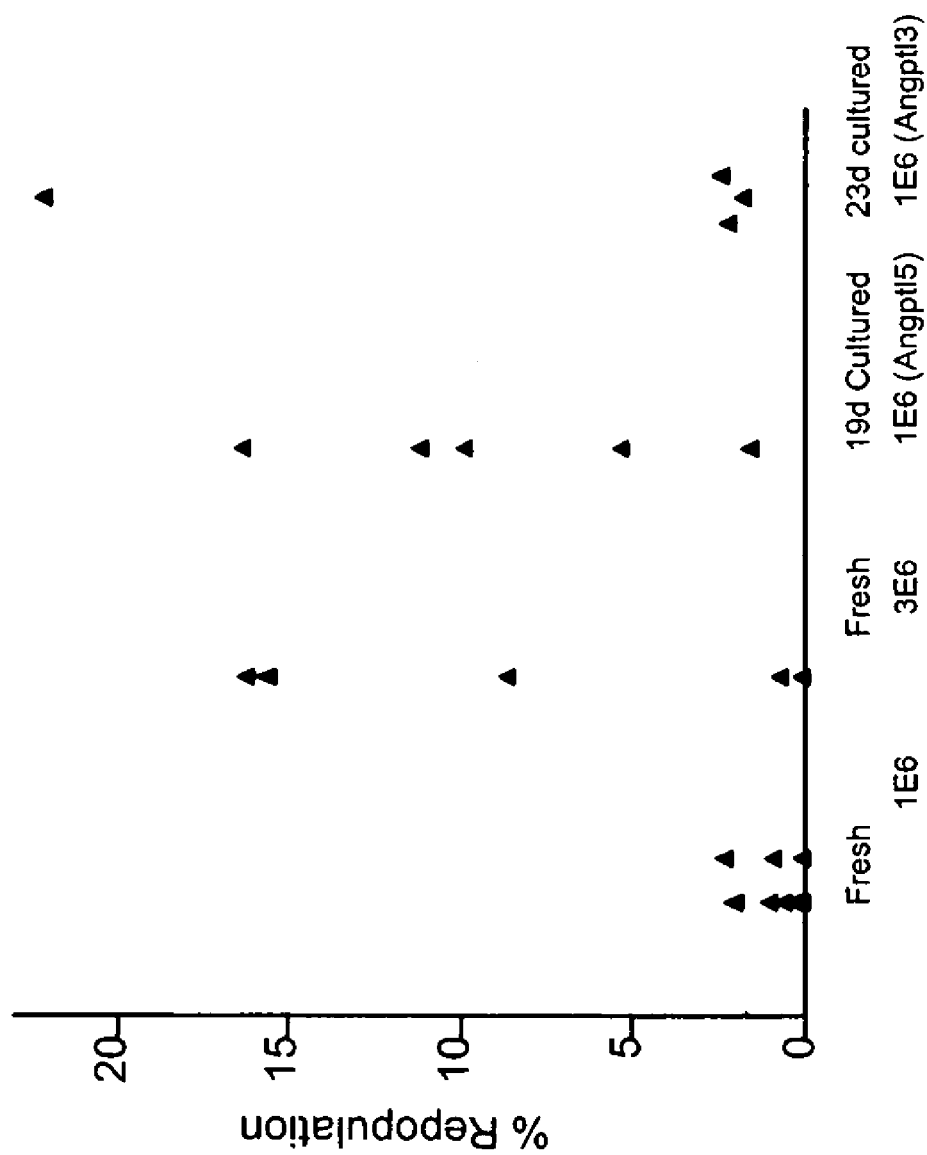
FIG. 13 is a graph showing percent repopulation in NOD/SCID recipient mice two months after transplant with human cord blood cells cultured for the indicated number of days in medium supplemented with the indicated growth factors.

As demonstrated in FIG. 13, culturing primary human cord blood cells in STIF medium supplemented with Angptl5 resulted in an approximately 3 fold increase in frequency of SCID mouse repopulating activity.

In conclusion, angiopoietin-like proteins are shown to be important novel growth factors for HSCs, including human HSCs. The stimulation of ex vivo expansion of HSCs by angiopoietin-like proteins most likely results from a direct effect of the hormone on these cells. As described herein, that the majority of freshly isolated LT-HSCs and all LT-HSCs cultured for 4 d bound Angptl2; thus the unknown receptor(s) of Angptl2 is expressed on cultured HSCs. Furthermore, the cultures described herein contained only 20 highly enriched HSCs in 160 µl of medium. Because of this low cell density, it is unlikely that any accessory cell(s) in this population respond to Angptl2 by producing sufficient amounts of other growth factors to stimulate HSC expansion.

A simple serum-free culture system for bone marrow HSCs using saturating levels of SCF, TPO, IGF-2, and FGF-1 was developed; during 10 d of culture of highly enriched HSCs an 8-fold increase in numbers of LT-HSCs was observed. (Zhang, C. C. & Lodish, H. F. Blood 105, 4314-20 (2005)). SCF, IGF-2, and FGF-1 all activate receptor protein-tyrosine kinases, whilst TPO signals through a member of the cytokine receptor superfamily that requires a Janus Kinase to activate intracellular signal transduction pathways. As demonstrated herein, addition of any of several members of the Angptl family—specifically Angptl2, Angptl3, Angptl, 4, Angptl5, and Angptl7, as well as Mfap4—result in a further increase in HSC activities. This suggests that the Angptls activate signal transduction pathways in addition to those activated by SCF, TPO, IGF-2, or FGF-1. As demonstrated herein, at least Angptl2 and Angptl3 are produced by HSC supportive mouse fetal liver CD3$^+$ cells; therefore, both Angptl2 and Angptl3 may normally function in vivo to stimulate expansion of fetal liver, and perhaps also adult, HSCs. As demonstrated by FIG. 13, Angptl5 stimulates human HSCs, demonstrating that Angptls are also an important growth factor family for human HSCs. Therefore, Angptls are useful for ex vivo expansion of HSCs. In addition, these factors are useful for ex vivo expansion of these cells as part of an HSC transplantation or gene therapy protocol.

It is to be understood that the description, specific examples and data, while indicating exemplary embodiments, are given by way of illustration and are not intended to limit the present invention. Various changes and modifications within the present invention will become apparent to the skilled artisan from the discussion, disclosure and data contained herein, and thus are considered part of the invention.

We claim:

1. A method of propagating hematopoietic stem cells (HSCs) in vitro comprising culturing a population of cells comprising HSCs in a culture medium comprising an angiopoietin-like protein and stem cell factor (SCF).

2. The method of claim 1, wherein the angiopoietin-like protein is selected from the group consisting of angiopoietin-like protein 2 and angiopoietin-like protein 3.

3. The method of claim 1, wherein the angiopoietin-like protein is selected from the group consisting of angiopoietin-like protein 4 and angiopoietin-like protein 5.

4. The method of claim 1, wherein the medium comprises between 0.1 ng and 500 ng angiopoietin-like protein per mL.

5. The method of claim 1, wherein the angiopoietin-like protein is recombinantly produced.

6. The method of claim 5, wherein the angiopoietin-like protein is glycosylated.

7. The method of claim 1, wherein the population of cells is cultured for at least five days.

8. The method of claim 1, wherein the population of cells is cultured for at least ten days.

9. The method of claim 1, wherein the culture medium is serum free medium.

10. The method of claim 9, wherein the culture medium further contains at least one additional factor selected from the group consisting of insulin-like growth factor (IGF), fibroblast growth factor (FGF), and thrombopoietin (TPO).

11. The method of claim 10, wherein the medium comprises between 0.1 ng and 500 ng of the additional factor per mL.

12. The method of claim 1, wherein the population of cells is selected from the group consisting of bone marrow cells, umbilical cord blood cells, and fetal liver cells.

13. The method of claim 1, wherein the population of cells are human cells.

14. The method of claim 1, wherein the population of cells are murine cells.

15. The method of claim 1, wherein the population of cells are primary cells.

16. The method of claim 1, wherein the population of cells comprises selected cells that bind to the angiopoietin-like protein, the method further comprising selecting said cells that bind to the angiopoietin-like protein prior to culturing the population of cells.

17. The method of claim 1, further comprising the step of selecting cells expressing at least one positive cell surface marker selected from the group consisting of Sca-1$^+$, CD45$^+$, IGF2-hFC$^+$, CD31$^+$, and Kit$^+$ and/or not expressing at least one negative cell surface marker selected from the group consisting of PrP, Lin, and CD62L after culturing the population of cells.

18. The method of claim 1, wherein the angiopoietin-like protein is selected from the group consisting of angiopoietin-like protein 3, angiopoietin-like protein 4, and angiopoietin-like protein 5.

19. The method of claim 1, wherein the culture medium comprises at least two of IGF, FGF, and TPO.

20. The method of claim 1, wherein the culture medium comprises at least three of IGF, FGF, and TPO.

21. The method of claim 1, wherein the culture medium comprises IGF, FGF, and TPO.

22. A method of propagating hematopoietic stem cells comprising culturing at least one primary hematopoietic stem cell for at least five days in a serum free culture medium comprising (i) an angiopoietin-like protein selected from the group consisting of angiopoietin-like protein 2, angiopoietin-like protein 3, angiopoietin-like protein 4, angiopoietin-like protein 5, angiopoietin-like protein 7, and Mfap4 and (ii) stem cell factor (SCF).

23. The method of claim 22, wherein the culture medium is serum free medium.

24. The method of claim 23, wherein the culture medium further comprises at least one additional factor selected from the group consisting of insulin-like growth factor (IGF), fibroblast growth factor (FGF), thrombopoietin (TPO).

25. The method of claim 22, wherein the one or more primary hematopoietic stem cells are selected from the group consisting of bone marrow cells, umbilical cord blood cells, and fetal liver cells.

26. The method of claim 22, wherein the one or more primary hematopoietic stem cells are human cells.

27. The method of claim 22, wherein the one or more primary hematopoietic stem cells are murine cells.

28. The method of claim 22, wherein the at least one primary hematopoietic stem cell comprise selected cells that bind to the angiopoietin-like protein, the method further comprising selecting said cells that bind to the angiopoietin-like protein prior to culturing the selected cells comprising at least one primary hematopoietic stem cell.

29. The method of claim 22, further comprising the step of selecting cells expressing at least one positive cell surface marker selected from the group consisting of Sca-1$^+$, CD45$^+$, IGF2-hFC$^+$, CD31$^+$, and Kit$^+$ and/or not expressing at least one negative cell surface marker selected from the group consisting of PrP, Lin, and CD62L after culturing the cells.

30. A method of propagating hematopoietic stem cells comprising culturing at least one human cell for at least five days in a serum free culture medium comprising angiopoietin-like protein 5 and stem cell factor (SCF), wherein at least one of the human cells is a hematopoietic stem cell.

31. The method of claim 30, wherein the culture medium is serum free medium.

32. The method of claim 30, wherein the culture medium further comprises at least one additional factor selected from the group consisting of insulin-like growth factor (IGF), fibroblast growth factor (FGF), thrombopoietin (TPO).

33. The method of claim 30, wherein the one or more human cells are selected from the group consisting of bone marrow cells and umbilical cord blood cells.

34. A method of administering hematopoietic stem cells to an individual comprising:
   a) obtaining hematopoietic stem cells from the individual or a donor;
   b) propagating the hematopoietic stem cells in a culture medium comprising an angiopoietin-like protein and stem cell factor (SCF), and
   c) transplanting the cultured cells into the individual.

35. The method of claim 34, wherein the culture medium is serum free medium.

36. The method of claim 34, wherein the angiopoietin-like protein is selected from the group consisting of angiopoietin-like protein 2, angiopoietin-like protein, angiopoietin-like protein 4, angiopoietin-like protein 5, angiopoietin-like protein 7, and Mfap4.

37. The method of claim 34, wherein the medium comprises between 0.1 ng and 500 ng of the angiopoietin-like protein per mL.

38. The method of claim 34, wherein the angiopoietin-like protein is recombinantly produced.

39. The method of claim 34, wherein the angiopoietin-like protein is glycosylated.

* * * * *

SEQUENCE LISTING

```
<160> NUMBER OF SEQ ID NOS: 6

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 1

Ile Glu Gly Arg Met Asp
  1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 2

Asp Tyr Lys Asp Asp Asp Asp Lys
  1               5

<210> SEQ ID NO 3
<211> LENGTH: 493
<212> TYPE: PRT
<213> ORGANISM: Homo sapiens

<400> SEQUENCE: 3

Met Arg Pro Leu Cys Val Thr Cys Trp Trp Leu Gly Leu Leu Ala Ala
  1               5                  10                  15

Met Gly Ala Val Ala Gly Gln Glu Asp Gly Phe Glu Gly Thr Glu Glu
                 20                  25                  30

Gly Ser Pro Arg Glu Phe Ile Tyr Leu Asn Arg Tyr Lys Arg Ala Gly
             35                  40                  45

Glu Ser Gln Asp Lys Cys Thr Tyr Thr Phe Ile Val Pro Gln Gln Arg
```

-continued

```
              50                  55                  60
Val Thr Gly Ala Ile Cys Val Asn Ser Lys Glu Pro Glu Val Leu Leu
 65                  70                  75                  80

Glu Asn Arg Val His Lys Gln Glu Leu Glu Leu Leu Asn Asn Glu Leu
                     85                  90                  95

Leu Lys Gln Lys Arg Gln Ile Glu Thr Leu Gln Gln Leu Val Glu Val
                100                 105                 110

Asp Gly Gly Ile Val Ser Glu Val Lys Leu Leu Arg Lys Glu Ser Arg
                115                 120                 125

Asn Met Asn Ser Arg Val Thr Gln Leu Tyr Met Gln Leu Leu His Glu
130                 135                 140

Ile Ile Arg Lys Arg Asp Asn Ala Leu Glu Leu Ser Gln Leu Glu Asn
145                 150                 155                 160

Arg Ile Leu Asn Gln Thr Ala Asp Met Leu Gln Leu Ala Ser Lys Tyr
                165                 170                 175

Lys Asp Leu Glu His Lys Tyr Gln His Leu Ala Thr Leu Ala His Asn
                180                 185                 190

Gln Ser Glu Ile Ile Ala Gln Leu Glu Glu His Cys Gln Arg Val Pro
                195                 200                 205

Ser Ala Arg Pro Val Pro Gln Pro Pro Ala Ala Pro Pro Arg Val
210                 215                 220

Tyr Gln Pro Pro Thr Tyr Asn Arg Ile Ile Asn Gln Ile Ser Thr Asn
225                 230                 235                 240

Glu Ile Gln Ser Asp Gln Asn Leu Lys Val Leu Pro Pro Pro Leu Pro
                245                 250                 255

Thr Met Pro Thr Leu Thr Ser Leu Pro Ser Ser Thr Asp Lys Pro Ser
                260                 265                 270

Gly Pro Trp Arg Asp Cys Leu Gln Ala Leu Glu Asp Gly His Asp Thr
                275                 280                 285

Ser Ser Ile Tyr Leu Val Lys Pro Glu Asn Thr Asn Arg Leu Met Gln
290                 295                 300

Val Trp Cys Asp Gln Arg His Asp Pro Gly Gly Trp Thr Val Ile Gln
305                 310                 315                 320

Arg Arg Leu Asp Gly Ser Val Asn Phe Phe Arg Asn Trp Glu Thr Tyr
                325                 330                 335

Lys Gln Gly Phe Gly Asn Ile Asp Gly Glu Tyr Trp Leu Gly Leu Glu
                340                 345                 350

Asn Ile Tyr Trp Leu Thr Asn Gln Gly Asn Tyr Lys Leu Leu Val Thr
                355                 360                 365

Met Glu Asp Trp Ser Gly Arg Lys Val Phe Ala Glu Tyr Ala Ser Phe
370                 375                 380

Arg Leu Glu Pro Glu Ser Glu Tyr Tyr Lys Leu Arg Leu Gly Arg Tyr
385                 390                 395                 400

His Gly Asn Ala Gly Asp Ser Phe Thr Trp His Asn Gly Lys Gln Phe
                405                 410                 415

Thr Thr Leu Asp Arg Asp His Asp Val Tyr Thr Gly Asn Cys Ala His
                420                 425                 430

Tyr Gln Lys Gly Gly Trp Trp Tyr Asn Ala Cys Ala His Ser Asn Leu
                435                 440                 445

Asn Gly Val Trp Tyr Arg Gly Gly His Tyr Arg Ser Arg Tyr Gln Asp
                450                 455                 460

Gly Val Tyr Trp Ala Glu Phe Arg Gly Gly Ser Tyr Ser Leu Lys Lys
465                 470                 475                 480
```

```
Val Val Met Met Ile Arg Pro Asn Pro Asn Thr Phe His
            485                 490
```

<210> SEQ ID NO 4
<211> LENGTH: 460
<212> TYPE: PRT
<213> ORGANISM: Homo sapiens

<400> SEQUENCE: 4

```
Met Phe Thr Ile Lys Leu Leu Phe Ile Val Pro Leu Val Ile Ser
  1               5                  10                  15

Ser Arg Ile Asp Gln Asp Asn Ser Ser Phe Asp Ser Leu Ser Pro Glu
                 20                  25                  30

Pro Lys Ser Arg Phe Ala Met Leu Asp Asp Val Lys Ile Leu Ala Asn
             35                  40                  45

Gly Leu Leu Gln Leu Gly His Gly Leu Lys Asp Phe Val His Lys Thr
 50                  55                  60

Lys Gly Gln Ile Asn Asp Ile Phe Gln Lys Leu Asn Ile Phe Asp Gln
 65                  70                  75                  80

Ser Phe Tyr Asp Leu Ser Leu Gln Thr Ser Glu Ile Lys Glu Glu Glu
                 85                  90                  95

Lys Glu Leu Arg Arg Thr Thr Tyr Lys Leu Gln Val Lys Asn Glu Glu
            100                 105                 110

Val Lys Asn Met Ser Leu Glu Leu Asn Ser Lys Leu Glu Ser Leu Leu
            115                 120                 125

Glu Glu Lys Ile Leu Leu Gln Gln Lys Val Lys Tyr Leu Glu Glu Gln
            130                 135                 140

Leu Thr Asn Leu Ile Gln Asn Gln Pro Glu Thr Pro Glu His Pro Glu
145                 150                 155                 160

Val Thr Ser Leu Lys Thr Phe Val Glu Lys Gln Asp Asn Ser Ile Lys
                165                 170                 175

Asp Leu Leu Gln Thr Val Glu Asp Gln Tyr Lys Gln Leu Asn Gln Gln
                180                 185                 190

His Ser Gln Ile Lys Glu Ile Glu Asn Gln Leu Arg Arg Thr Ser Ile
            195                 200                 205

Gln Glu Pro Thr Glu Ile Ser Leu Ser Ser Lys Pro Arg Ala Pro Arg
            210                 215                 220

Thr Thr Pro Phe Leu Gln Leu Asn Glu Ile Arg Asn Val Lys His Asp
225                 230                 235                 240

Gly Ile Pro Ala Glu Cys Thr Thr Ile Tyr Asn Arg Gly Glu His Thr
                245                 250                 255

Ser Gly Met Tyr Ala Ile Arg Pro Ser Asn Ser Gln Val Phe His Val
            260                 265                 270

Tyr Cys Asp Val Ile Ser Gly Ser Pro Trp Thr Leu Ile Gln His Arg
            275                 280                 285

Ile Asp Gly Ser Gln Asn Phe Asn Glu Thr Trp Glu Asn Tyr Lys Tyr
            290                 295                 300

Gly Phe Gly Arg Leu Asp Gly Glu Phe Trp Leu Gly Leu Glu Lys Ile
305                 310                 315                 320

Tyr Ser Ile Val Lys Gln Ser Asn Tyr Val Leu Arg Ile Glu Leu Glu
                325                 330                 335

Asp Trp Lys Asp Asn Lys His Tyr Ile Glu Tyr Ser Phe Tyr Leu Gly
            340                 345                 350

Asn His Glu Thr Asn Tyr Thr Leu His Leu Val Ala Ile Thr Gly Asn
```

-continued

```
                355                 360                 365
Val Pro Asn Ala Ile Pro Glu Asn Lys Asp Leu Val Phe Ser Thr Trp
    370                 375                 380

Asp His Lys Ala Lys Gly His Phe Asn Cys Pro Glu Gly Tyr Ser Gly
385                 390                 395                 400

Gly Trp Trp Trp His Asp Glu Cys Gly Glu Asn Asn Leu Asn Gly Lys
                405                 410                 415

Tyr Asn Lys Pro Arg Ala Lys Ser Lys Pro Glu Arg Arg Arg Gly Leu
                420                 425                 430

Ser Trp Lys Ser Gln Asn Gly Arg Leu Tyr Ser Ile Lys Ser Thr Lys
                435                 440                 445

Met Leu Ile His Pro Thr Asp Ser Glu Ser Phe Glu
    450                 455                 460

<210> SEQ ID NO 5
<211> LENGTH: 406
<212> TYPE: PRT
<213> ORGANISM: Homo sapiens

<400> SEQUENCE: 5

Met Ser Gly Ala Pro Thr Ala Gly Ala Ala Leu Met Leu Cys Ala Ala
  1               5                  10                  15

Thr Ala Val Leu Leu Ser Ala Gln Gly Gly Pro Val Gln Ser Lys Ser
                 20                  25                  30

Pro Arg Phe Ala Ser Trp Asp Glu Met Asn Val Leu Ala His Gly Leu
             35                  40                  45

Leu Gln Leu Gly Gln Gly Leu Arg Glu His Ala Glu Arg Thr Arg Ser
     50                  55                  60

Gln Leu Ser Ala Leu Glu Arg Arg Leu Ser Ala Cys Gly Ser Ala Cys
 65                  70                  75                  80

Gln Gly Thr Glu Gly Ser Thr Asp Leu Pro Leu Ala Pro Glu Ser Arg
                 85                  90                  95

Val Asp Pro Glu Val Leu His Ser Leu Gln Thr Gln Leu Lys Ala Gln
             100                 105                 110

Asn Ser Arg Ile Gln Gln Leu Phe His Lys Val Ala Gln Gln Gln Arg
         115                 120                 125

His Leu Glu Lys Gln His Leu Arg Ile Gln His Leu Gln Ser Gln Phe
    130                 135                 140

Gly Leu Leu Asp His Lys His Leu Asp His Glu Val Ala Lys Pro Ala
145                 150                 155                 160

Arg Arg Lys Arg Leu Pro Glu Met Ala Gln Pro Val Asp Pro Ala His
                165                 170                 175

Asn Val Ser Arg Leu His Arg Leu Pro Arg Asp Cys Gln Glu Leu Phe
            180                 185                 190

Gln Val Gly Glu Arg Gln Ser Gly Leu Phe Glu Ile Gln Pro Gln Gly
        195                 200                 205

Ser Pro Pro Phe Leu Val Asn Cys Lys Met Thr Ser Asp Gly Gly Trp
    210                 215                 220

Thr Val Ile Gln Arg Arg His Asp Gly Ser Val Asp Phe Asn Arg Pro
225                 230                 235                 240

Trp Glu Ala Tyr Lys Ala Gly Phe Gly Asp Pro His Gly Glu Phe Trp
                245                 250                 255

Leu Gly Leu Glu Lys Val His Ser Ile Thr Gly Asp Arg Asn Ser Arg
            260                 265                 270
```

```
Leu Ala Val Gln Leu Arg Asp Trp Asp Gly Asn Ala Glu Leu Leu Gln
            275                 280                 285

Phe Ser Val His Leu Gly Gly Glu Asp Thr Ala Tyr Ser Leu Gln Leu
            290                 295                 300

Thr Ala Pro Val Ala Gly Gln Leu Gly Ala Thr Thr Val Pro Pro Ser
305                 310                 315                 320

Gly Leu Ser Val Pro Phe Ser Thr Trp Asp Gln Asp His Asp Leu Arg
                325                 330                 335

Arg Asp Lys Asn Cys Ala Lys Ser Leu Ser Gly Gly Trp Trp Phe Gly
            340                 345                 350

Thr Cys Ser His Ser Asn Leu Asn Gly Gln Tyr Phe Arg Ser Ile Pro
            355                 360                 365

Gln Gln Arg Gln Lys Leu Lys Lys Gly Ile Phe Trp Lys Thr Trp Arg
            370                 375                 380

Gly Arg Tyr Tyr Pro Leu Gln Ala Thr Thr Met Leu Ile Gln Pro Met
385                 390                 395                 400

Ala Ala Glu Ala Ala Ser
            405

<210> SEQ ID NO 6
<211> LENGTH: 388
<212> TYPE: PRT
<213> ORGANISM: Homo sapiens

<400> SEQUENCE: 6

Met Met Ser Pro Ser Gln Ala Ser Leu Leu Phe Leu Asn Val Cys Ile
1               5                   10                  15

Phe Ile Cys Gly Glu Ala Val Gln Gly Asn Cys Val His His Ser Thr
            20                  25                  30

Asp Ser Ser Val Val Asn Ile Val Glu Asp Gly Ser Asn Ala Lys Asp
        35                  40                  45

Glu Ser Lys Ser Asn Asp Thr Val Cys Lys Glu Asp Cys Glu Glu Ser
    50                  55                  60

Cys Asp Val Lys Thr Lys Ile Thr Arg Glu Glu Lys His Phe Met Cys
65                  70                  75                  80

Arg Asn Leu Gln Asn Ser Ile Val Ser Tyr Thr Arg Ser Thr Lys Lys
                85                  90                  95

Leu Leu Arg Asn Met Met Asp Glu Gln Gln Ala Ser Leu Asp Tyr Leu
            100                 105                 110

Ser Asn Gln Val Asn Glu Leu Met Asn Arg Val Leu Leu Leu Thr Thr
            115                 120                 125

Glu Val Phe Arg Lys Gln Leu Asp Pro Phe Pro His Arg Pro Val Gln
        130                 135                 140

Ser His Gly Leu Asp Cys Thr Asp Ile Lys Asp Thr Ile Gly Ser Val
145                 150                 155                 160

Thr Lys Thr Pro Ser Gly Leu Tyr Ile Ile His Pro Glu Gly Ser Ser
                165                 170                 175

Tyr Pro Phe Glu Val Met Cys Asp Met Asp Tyr Arg Gly Gly Gly Trp
            180                 185                 190

Thr Val Ile Gln Lys Arg Ile Asp Gly Ile Asp Phe Gln Arg Leu
            195                 200                 205

Trp Cys Asp Tyr Leu Asp Gly Phe Gly Asp Leu Leu Gly Glu Phe Trp
        210                 215                 220

Leu Gly Leu Lys Lys Ile Phe Tyr Ile Val Asn Gln Lys Asn Thr Ser
225                 230                 235                 240
```

```
-continued

Phe Met Leu Tyr Val Ala Leu Glu Ser Glu Asp Asp Thr Leu Ala Tyr
            245             250                 255

Ala Ser Tyr Asp Asn Phe Trp Leu Glu Asp Glu Thr Arg Phe Phe Lys
            260             265                 270

Met His Leu Gly Arg Tyr Ser Gly Asn Ala Gly Asp Ala Phe Arg Gly
        275             280             285

Leu Lys Lys Glu Asp Asn Gln Asn Ala Met Pro Phe Ser Thr Ser Asp
    290             295             300

Val Asp Asn Asp Gly Cys Arg Pro Ala Cys Leu Val Asn Gly Gln Ser
305             310             315             320

Val Lys Ser Cys Ser His Leu His Asn Lys Thr Gly Trp Trp Phe Asn
                325             330             335

Glu Cys Gly Leu Ala Asn Leu Asn Gly Ile His His Phe Ser Gly Lys
            340             345             350

Leu Leu Ala Thr Gly Ile Gln Trp Gly Thr Trp Thr Lys Asn Asn Ser
        355             360             365

Pro Val Lys Ile Lys Ser Val Ser Met Lys Ile Arg Arg Met Tyr Asn
    370             375             380

Pro Tyr Phe Lys
385
```